United States Patent
Stolen et al.

(10) Patent No.: US 10,188,353 B2
(45) Date of Patent: Jan. 29, 2019

(54) SYSTEMS AND METHODS FOR MONITORING AUTONOMIC HEALTH

(71) Applicant: Cardiac Pacemakers, Inc., St. Paul, MN (US)

(72) Inventors: Craig Stolen, New Brighton, MN (US); Stephen B. Ruble, Lino Lakes, MN (US); Rahul Agarwal, Baltimore, MD (US); Nicholas Wold, Arden Hills, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 12 days.

(21) Appl. No.: 15/273,302

(22) Filed: Sep. 22, 2016

(65) Prior Publication Data
US 2017/0079598 A1    Mar. 23, 2017

Related U.S. Application Data

(60) Provisional application No. 62/222,005, filed on Sep. 22, 2015.

(51) Int. Cl.
*A61N 1/00* (2006.01)
*A61B 5/00* (2006.01)
(Continued)

(52) U.S. Cl.
CPC .......... *A61B 5/7275* (2013.01); *A61B 5/0215* (2013.01); *A61B 5/02405* (2013.01);
(Continued)

(58) Field of Classification Search
CPC .............. A61B 5/0215; A61B 5/02405; A61B 5/04001; A61B 5/0402; A61B 5/0456;
(Continued)

(56) References Cited

U.S. PATENT DOCUMENTS

2003/0078623 A1* 4/2003 Weinberg ............... A61N 1/056
                                                            607/9
2006/0241562 A1* 10/2006 John ..................... A61B 5/048
                                                          604/503
(Continued)

FOREIGN PATENT DOCUMENTS

CN      107073217 A    8/2017
JP        6296613 A   10/1994
(Continued)

OTHER PUBLICATIONS

"International Application Serial No. PCT/US2015/055240, International Search Report dated Feb. 8, 2016", 4 pgs.
(Continued)

*Primary Examiner* — George Manuel
(74) *Attorney, Agent, or Firm* — Schwegman Lundberg & Woessner, P.A.

(57) ABSTRACT

A system for monitoring autonomic health may include an autonomic nerve stimulation (ANS) dose delivery system and a response extractor. The response extractor may be configured to record physiological parameter values including first population data that includes evoked response (ER) values corresponding to evoked physiological responses, and second population data that includes reference values that include no effect (NE) values corresponding to times without a physiological response. The response monitor may calculate evoked response metrics (ERMs) using the first and second population data where each of the ERMs may be dependent on background autonomic activity. The response extractor may analyze the ERMs to provide ERM analysis, and provide an indication of autonomic health using the ERM analysis.

20 Claims, 27 Drawing Sheets

(51) Int. Cl.

| | |
|---|---|
| *A61B 5/0215* | (2006.01) |
| *A61B 5/024* | (2006.01) |
| *A61B 5/08* | (2006.01) |
| *A61N 1/36* | (2006.01) |
| *A61B 5/0402* | (2006.01) |
| *A61B 5/04* | (2006.01) |
| *A61N 1/05* | (2006.01) |
| *A61N 1/04* | (2006.01) |
| *A61B 5/0456* | (2006.01) |

(52) U.S. Cl.
CPC ........ *A61B 5/04001* (2013.01); *A61B 5/0402* (2013.01); *A61B 5/0816* (2013.01); *A61B 5/4035* (2013.01); *A61B 5/4848* (2013.01); *A61N 1/36053* (2013.01); *A61N 1/36114* (2013.01); *A61N 1/36139* (2013.01); *A61B 5/0456* (2013.01); *A61N 1/0456* (2013.01); *A61N 1/0551* (2013.01); *A61N 1/36117* (2013.01); *A61N 1/36178* (2013.01)

(58) Field of Classification Search
CPC ... A61B 5/0816; A61B 5/4035; A61B 5/4848; A61B 5/7275; A61N 1/0456; A61N 1/0551; A61N 1/36053; A61N 1/36114; A61N 1/36117; A61N 1/36139; A61N 1/36178
See application file for complete search history.

(56) References Cited

U.S. PATENT DOCUMENTS

| | | |
|---|---|---|
| 2010/0191311 A1 | 7/2010 | Scheiner et al. |
| 2011/0040348 A1 | 2/2011 | Wacnik et al. |
| 2011/0257708 A1 | 10/2011 | Kramer et al. |
| 2013/0053926 A1 | 2/2013 | Hincapie Ordonez et al. |
| 2015/0157867 A1 | 6/2015 | Ternes et al. |
| 2016/0101289 A1 | 4/2016 | Stolen et al. |

FOREIGN PATENT DOCUMENTS

| | | |
|---|---|---|
| WO | WO-2010051499 A1 | 5/2010 |
| WO | WO-2016061045 A1 | 4/2016 |
| WO | WO-2017053504 A1 | 3/2017 |

OTHER PUBLICATIONS

"International Application Serial No. PCT/US2015/055240, Written Opinion dated Feb. 8, 2016", 4 pgs.

Bohm, M., et al., "Heart rate as a risk factor in chronic heart failure (SHIFT): the association between heart rate and outcomes in a randomised placebo-controlled trial", Lancet 2010; 376, (Aug. 29, 210), 886-894.

Bohm, M., et al., "Twenty-four-hour heart rate lowering with ivabradine in chronic heart failure: insights from the SHIFT Holter substudy", European Journal of Heart Failure (2015) 17, (Mar. 2015), 518-526.

Borovikova, L V, et al., "Vagus nerve stimulation attenuates the systemic inflammatory response to endotoxin", Nature | vol. 405, (May 25, 2000), 458-462.

De Ferrari, G. M., et al., "Chronic vagus nerve stimulation: a new and promising therapeutic approach for chronic heart failure", European Heart Journal (2011) 32,, (Oct. 2010), 847-855.

De Ferrari, G. M., "Vagal Stimulation in Heart Failure", J. of Cardiovasc. Trans. Res. (2014) 7, (2014), 310-320.

Fox, Kim, et al., "Resting Heart Rate in Cardiovascular Disease", Journal of American College of Cardiology; vol. 50; No. 9, (2007), 823-830.

Hamann, J. J., et al., "Vagus nerve stimulation improves left ventricular function in a canine model of chronic heart failure", European Journal of Heart Failure (2013) 15, (2013), 1319-1326.

Hauptman, Paul J., et al., "Rationale and study design of the INcrease of Vagal Tone in Heart Failure study: INOVATE-HF", American Heart Journal, vol. 163, No. 6, (Jun. 2012), 954-962.

Levy, M., "Sympathetic-Parasympathetic Interactions in the Heart", Circulation Research; vol. XXIX, No. 5, (Nov. 1971), 437-445.

Li, Meihua, et al., "Vagal Nerve Stimulation Markedly Improves Long-Term Survival After Chronic Heart Failure in Rats", AMA; Circulation;, (2004), 120-124.

Premchand, R K., "Autonomic Regulation Therapy via Left or Right Cervical Vagus Nerve Stimulation in Patients With Chronic Heart Failure: Results of the ANTHEM-HF Trial", J. of Cardiac Failure; vol. 20; No. 11, (2014), 808-816.

Sabbah, H. N., et al., "Therapy with Vagus nerve electrical stimulation combined with beta-blockade improves left ventricular systolic function in dogs with heart failure beyond that seen with beta-blockade alone", European Journal of Heart Failure Supplements; 6, (2007), 114.

Sabbah, Hani N., et al., "Vagus Nerve Stimulation in Experimental Heart Failure", Heart Fail Rev.; 16(2), (Mar. 2011), 171-178.

Woodbury, Dixon, et al., "Effects of Vagal Stimulation on Experimentally Induced Seizures in Rats", Epilepsia, 31(Suppl. 2), (1990), S7-S19.

Zannad, Faiez, et al., "Chronic vagal stimulation for the treatment of low ejection fraction heart failure: results of the neural cardiac therapy for heart failure (NECTAR-HF) randomized controlled trial", European Heart Journal; 36;, (2015), 425-433.

Zhang, Y., et al., "Chronic Vagus Nerve Stimulation Improves Autonomic Control and Attenuates Systemic Inflammation and Heart Failure Progression in a Canine High-Rate Pacing Model", Circ Heart Fail. 2009; 2, (Jul. 2009), 692-699.

"U.S. Appl. No. 14/881,574, Final Office Action dated Nov. 7, 2017", 9 pgs.

"U.S. Appl. No. 14/881,574, Non Final Office Action dated Feb. 2, 2018", 9 pgs.

"U.S. Appl. No. 14/881,574, Non Final Office Action dated Jun. 20, 2017", 10 pgs.

"U.S. Appl. No. 14/881,574, Response filed Jan. 15, 2018 to Final Office Action dated Nov. 7, 2017", 10 pgs.

"U.S. Appl. No. 14/881,574, Response filed May 1, 2017 to Restriction Requirement dated Mar. 9, 2017", 8 pgs.

"U.S. Appl. No. 14/881,574, Response filed Sep. 19, 2017 to Non Final Office Action dated Jun. 20, 2017", 9 pgs.

"U.S. Appl. No. 14/881,574, Restriction Requirement dated Mar. 9, 2017", 6 pgs.

"European Application Serial No. 15795254.0, Response filed Dec. 21, 2017 to Communication Pursuant to Rules 161 and 162 EPC dated Jun. 19, 2017", 16 pgs.

"International Application Serial No. PCT/US2015/055240, International Preliminary Report on Patentability dated Apr. 27, 2017", 6 pgs.

"International Application Serial No. PCT/US2016/052999, International Search Report dated Feb. 2, 2017", 4 pgs.

"International Application Serial No. PCT/US2016/052999, Written Opinion dated Feb. 2, 2017", 5 pgs.

U.S. Appl. No. 14/881,574, filed Oct. 13, 2015, Systems and Methods for Delivering Vagal Therapy.

"International Application Serial No. PCT/US2016/052999, International Preliminary Report on Patentability dated Apr. 5, 2018", 7 pgs.

\* cited by examiner

SYSTEMS AND METHODS FOR MONITORING AUTONOMIC HEALTH

CLAIM OF PRIORITY

This application claims the benefit of priority under 35 U.S.C. § 119(e) of U.S. Provisional Patent Application Ser. No. 62/222,005, filed on Sep. 22, 2015, which is herein incorporated by reference in its entirety.

TECHNICAL FIELD

This application relates generally to medical systems and methods and, more particularly, to systems and methods for monitoring autonomic health.

BACKGROUND

The automatic nervous system (ANS) regulates "involuntary" organs and maintains normal internal function and works with the somatic nervous system. The ANS includes the sympathetic nervous system and the parasympathetic nervous system. The sympathetic nervous system is affiliated with stress and the "fight or flight response" to emergencies, and the parasympathetic nervous system is affiliated with relaxation and the "rest and digest response."

Autonomic balance reflects the relationship between parasympathetic and sympathetic activity. Autonomic balance may sometimes be referred to as autonomic tone, which refers to a background rate of activity of the ANS. Changes in autonomic balance are reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example. It is desirable to monitor autonomic health as overall health depends on a healthy autonomic balance.

SUMMARY

Various embodiments monitor autonomic health by delivering a dose of neural stimulation and monitoring subtle, inconsistent physiological responses that have a dependence on background autonomic activity. These responses may be inconsistent as they may only be present for a fraction of the time and further may be a relatively small response. The dose of neural stimulation may be less than that which would drive an acutely-obvious, physiologic response.

Given the complexity of the ANS and interrelation with many physiological functions, these subtle, inconsistent responses are not detectable simply by observing an acute heart rate or blood pressure response. Rather, the subtle, inconsistent responses to the dose of neural stimulation may be detected using statistical techniques to provide an evoked response metric (ERM) such as a T-score or Z-score. These subtle, inconsistent physiological responses to the dose of neural stimulation may have a dependence on the background autonomic activity of the patient, and thus may be used to monitor, by way of example, therapy effectiveness, patient-compliance, or disease progression. Various embodiments may monitor changes in contractility, such as may be used to monitor Cardiac Contractility Modulation (CCM). CCM applied with a regular ON/OFF cycle may be detected if CCM changes contraction intensity or rate either directly or through a neuro mechanism.

An example (e.g. "Example 1") of a system for monitoring autonomic health of a person may include an autonomic nerve stimulation (ANS) dose delivery system and a response extractor. The ANS dose delivery system may be configured to provide an ANS dose using stimulation pulses to stimulate autonomic neural tissue at a programmed stimulation dose. The ANS dose delivery system may include a pulse generator configured to generate stimulation pulses and a controller operably connected to the pulse generator to control the pulse generator to provide the ANS dose. The response extractor is configured to record physiological parameter values, where the physiologic parameter values include first population data that includes evoked response (ER) values corresponding to evoked physiological responses, and second population data that includes reference values that include no effect (NE) values corresponding to times without a physiological response. The response monitor may calculate evoked response metrics (ERMs) using the first and second population data. Each of the ERMs may be dependent on background autonomic activity. The response extractor may analyze the ERMs to provide ERM analysis, and provide an indication of autonomic health using the ERM analysis.

In Example 2, the subject matter of Example 1 may optionally be configured such that the ANS dose delivery system is configured to deliver intermittent ANS that includes a plurality of stimulation bursts wherein each stimulation burst includes a plurality of neural stimulation pulses and successive neural stimulation bursts are separated by a time without neural stimulation pulses. The response extractor may be configured to record ER values corresponding to the evoked physiological responses to stimulation bursts and reference values that include NE values corresponding to physiological parameter values that are not evoked physiological responses to stimulation bursts, and Z-score or T-score the recorded physiological parameter values to obtain a group of ER Z-scores or ER T-scores, wherein the ERMs include the group of ER Z-scores or ER T-scores.

In Example 3, the subject matter of any one or any combination of Examples 1-2 may optionally be configured such that the response extractor is configured to compare the ERMs to at least one reference value to monitor autonomic health.

In Example 4, the subject matter of any one or any combination of Examples 1-3 may optionally be configured such that the response extractor is configured to trend the ERMs to monitor autonomic health.

In Example 5, the subject matter of any one or any combination of Examples 1-4 may optionally be configured such that the ANS dose delivery system is configured to adjust the ANS dose in steps, and the response extractor is configured to calculate an ERM for each step and compare the ERM to a reference value to monitor autonomic health.

In Example 6, the subject matter of any one or any combination of Examples 1-5 may optionally be configured such that the ER values include stimulation effect (SE) values corresponding to direct responses to stimulation bursts, and the response extractor configured to calculate ERMs using the SE scores and the second population.

In Example 7, the subject matter of any one or any combination of Examples 1-6 may optionally be configured such that the system is configured to detect a condition, and the response extractor is configured to be at least partially disabled in response to the detected condition or is configured to be at least partially enabled in response to the detected condition.

In Example 8, the subject matter of any one or any combination of Examples 1-7 may optionally be configured such that the system includes a patient status or condition detector. The response extractor may be configured to tag the ERMs with the detected patient status or condition.

In Example 9, the subject matter of any one or any combination of Examples 1-8 may optionally be configured such that the response extractor is configured to record stimulation effect (SE) values corresponding to direct responses to delivered stimulation pulses or reflex effect (RE) values corresponding to reflex responses after delivered stimulation pulses, or both SE values and RE values.

In Example 10, the subject matter of any one or any combination of Examples 1-9 may optionally be configured such that the ANS dose delivery system is configured to deliver bursts of neural stimulation pulses, and the response extractor is configured to record NE values that include values during times between successive bursts of neural stimulation pulses.

In Example 11, the subject matter of any one or any combination of Examples 1-10 may optionally be configured such that the physiological parameter values include at least one of: heart rate values or heart rate variability values.

In Example 1 the subject matter of any one or any combination of Examples 1-11 may optionally be configured such that the physiological parameter values include at least one of: blood pressure values or blood pressure variability values.

In Example 13, the subject matter of any one or any combination of Examples 1-12 may optionally be configured such that the physiological parameter values include at least one of respiratory values or respiratory variability values.

In Example 14, the subject matter of any one or any combination of Examples 1-13 may optionally be configured such that the response extractor is configured to record electrocardiograms (ECGs), and to calculate ERMs using a statistical analysis of at least one feature of the ECGs to calculate ERMs.

In Example 15, the subject matter of any one or any combination of Examples 1-14 may optionally be configured such that the ANS dose delivery system is configured to deliver a vagal nerve stimulation (VNS) dose. The ERMs may include a sympathetic reflex effect (RE) to the VNS dose, and larger ERMs indicate higher background sympathetic activity and lower ERMs indicate lower background sympathetic activity.

An example (e.g. "Example 16") of a method may include delivering an autonomic neural stimulation (ANS) dose, which may include delivering stimulation pulses to evoke physiological responses. The method may further include recording physiological parameter values, which may include recording first population data, the first population data including evoked response (ER) values corresponding to the evoked physiological responses, and recording second population data, the second population data including reference values that include no effect (NE) values corresponding to times without an evoked physiological response. The method may further include calculating evoked response metrics (ERMs) using the first and second population data, each of the ERMs being dependent on background autonomic activity, analyzing the ERMs to provide ERM analysis, and providing an indication of autonomic health using the ERM analysis. A system may be configured to implement the method. The system may include hardware, software, firmware, or any combination thereof to implement the method. In implementing the method, the system may use a set (or sets) of instructions contained on a computer accessible medium (or media) capable of directing a processor or other controller to perform at least a portion of the method.

In Example 17, the subject matter of Example 16 may optionally be configured such that analyzing the ERMs includes comparing the ERMs to at least one reference value to provide the ERM analysis used to provide the indication of autonomic health.

In Example 18, the subject matter of any one or any combination of Examples 16-17 may optionally be configured such that analyzing the ERMs includes trending the ERMs to provide the ERM analysis used to provide the indication of autonomic health.

In Example 19, the subject matter of any one or any combination of Examples 16-18 may optionally be configured such that the ER values include stimulation effect (SE) values corresponding to direct responses to delivered stimulation pulses, or reflex effect (RE) values corresponding to reflex responses after delivered stimulation pulses, or both SE values and RE values.

In Example 20, the subject matter of any one or any combination of Examples 16-19 may optionally be configured such that delivering the ANS dose includes delivering bursts of neural stimulation pulses. The NE values may include values during times between successive bursts of neural stimulation pulses.

In Example 21, the subject matter of any one or any combination of Examples 16-20 may optionally be configured such that the physiological parameter values include at least one of: heart rate values or heart rate variability values.

In Example 22, the subject matter of any one or any combination of Examples 16-21 may optionally be configured such that the physiological parameter values include at least one of: respiratory values or respiratory variability values.

In Example 23, the subject matter of any one or any combination of Examples 16-22 may optionally be configured such that the physiological parameter values include at least one of: blood pressure values or blood pressure variability values.

In Example 24, the subject matter of any one or any combination of Examples 16-23 may optionally be configured such that recording physiological parameter values includes recording electrocardiograms (ECGs), and calculating ERMs includes calculating ERMs using a statistical analysis of at least one feature of the ECGs.

In Example 25, the subject matter of any one or any combination of Examples 16-24 may optionally be configured such that calculating ERMs includes Z-scoring groups of recorded physiological parameter values to obtain Z-scores for each of the groups, or T-scoring groups of recorded physiological parameter values to obtain T-scores for each of the groups.

In Example 26, the subject matter of any one or any combination of Examples 16-25 may optionally be configured such that delivering the ANS dose includes delivering neural stimulation to a vagus nerve.

In Example 27, the subject matter of any one or any combination of Examples 16-26 may optionally be configured such that delivering the ANS dose includes delivering neural stimulation to a carotid sinus nerve or a glossopharyngeal nerve.

In Example 28, the subject matter of any one or any combination of Examples 16-26 may optionally be configured such that delivering the ANS dose includes delivering neural stimulation to a baroreceptor region or to a chemoreceptor region.

An example (e.g. "Example 29") of a method may include delivering a vagal nerve stimulation (VNS) dose and sensing heart rate and recording heart rate values. The VNS dose may include a plurality of stimulation bursts. Each stimulation burst may include a plurality of neural stimulation pulses, and successive neural stimulation bursts are separated by a time without neural stimulation pulses. Sensing heart rate and recording heart rate values may include recording first population data and second population data. The first population data may include evoked response (ER) values corresponding to the evoked heart rate effects to stimulation bursts. The second population data may include reference values that include no effect (NE) values corresponding to heart rate values that are not evoked heart rate responses to stimulation bursts. The method may include calculating evoked response metrics (ERMs) to quantify a relationship between the first population data and the second population data. Each of the ERMs may be dependent on background sympathetic activity. The method may further include analyzing the ERMs to provide ERM analysis, and providing an indication of autonomic health using the ERM analysis. A system may be configured to implement the method. The system may include hardware, software, firmware, or any combination thereof to implement the method. In implementing the method, the system may use a set (or sets) of instructions contained on a computer accessible medium (or media) capable of directing a processor or other controller to perform at least a portion of the method.

In Example 30, the subject matter of Example 29 may optionally be configured such that the method further includes adjusting the ANS dose in steps, calculating an ERM for each step and comparing the ERM to a reference value to monitor autonomic health.

In Example 31, the subject matter of any one or any combination of Examples 29-30 may optionally be configured such that analyzing the ERMs includes comparing the ERMs to at least one reference value to provide the ERM analysis used to provide the indication of autonomic health.

In Example 32 the subject matter of any one or any combination of Examples 29-31 may optionally be configured such that analyzing the ERMs includes trending the ERMs to provide the ERM analysis used to provide the indication of autonomic health.

In Example 33, the subject matter of any one or any combination of Examples 29-32 may optionally be configured such that the method further includes detecting a patient status or a patient condition, and tagging the ERMs with the detected patient status or condition.

In Example 34, the subject matter of any one or any combination of Examples 29-33 may optionally be configured such that the ER values in the first population data includes stimulation effect (SE) values corresponding to direct responses to stimulation bursts, and calculating ERMs includes analyzing for a SE signature.

In Example 35, the subject matter of any one or any combination of Examples 29-34 may optionally be configured such that the ER values in the first population data include reflex effect (RE) values corresponding to reflex responses after stimulation bursts, and calculating the ERM to quantify the relationship between the first population data and the second population data includes analyzing for a RE signature.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIG. 6B illustrates a direct and reflex response of the circulation (e.g., heart rate decrease then increase or blood pressure decrease then increase) to the parasympathetic stimulation pulse train, as illustrated in FIG. 4, at an efferent parasympathetic target as illustrated in FIG. 6A.

DETAILED DESCRIPTION

Figure 1:
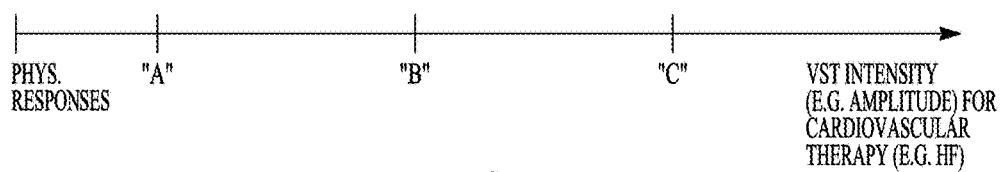
FIG. 1 illustrates increasing VNS intensity from the left side to the right side of the figure, and further illustrates intensity thresholds that elicit various physiological responses to VNS.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The ANS regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating or inhibiting the sympathetic or parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Examples of such diseases or conditions include HF, hypertension, and cardiac remodeling. These conditions are briefly described below. Autonomic neurostimulation may be used to stimulate or inhibit autonomic neural targets in the patient. By way of example and not limitation, autonomic neural targets may include the vagus nerve including various locations along the vagus nerve such as the cervical region and cardiac nerves, the carotid sinus nerve, the glossopharyngeal nerve, baroreceptors, chemoreceptors, fat pads spinal cord, and nerve roots. Medicines, such as beta blockers, may be used to adjust autonomic balance.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have reduced autonomic balance, which is associated with LV dysfunction and increased mortality.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

By way of example, vagal stimulation therapy (VST) has been proposed to treat various cardiovascular diseases, including HF. VST is being investigated a potential therapy for heart failure amelioration. Efferent and afferent vagus nerve fibers modulate heart rate through direct innervation of the SA node and centrally though a modulation of the sympathetic and parasympathetic balance. Acute VST can decrease heart rate and chronic VNS can blunt heart failure progression in pre-clinical models. Early VNS studies intentionally decreased heart rate and found a reduction in post MI mortality. However, VST-induced bradycardia could cause symptomatic side effects for HF patients, especially during exercise, and could provide undesired inotropic and dromotropic effects. It is believed that beneficial effects of VST on cardiac function and remodeling are not necessarily mediated via significant heart rate reduction that is acutely observable. That is, VST can benefit HF patients without the undesired chronotropic effects associated with VST as well as other side effects due to high intensity stimulation such as coughing, etc. Rather, anti-inflammatory, anti-sympathetic, and anti-apoptosis mediators are triggered at lower VST intensities than intensities at which a heart rate reduction is realized. These mediators function as pathways through which the VST provides the therapeutic effects for cardiovascular disease. Vagal nerve signaling plays an important role in modulating systemic inflammatory response and apoptosis, which are important in the development and progression of HF. Low level of efferent vagal nerve stimulation (1 Hz) has been shown to attenuate the release of proinflammatory cytokines (such as tumor necrosis factor, interleukin, etc.) from macrophage through nicotinic acetylcholine receptors (see *Borovikova, LV. Nature.* 2000, 405: 458-462). Our internal preclinical data suggests that the therapeutic level of VST could modulate inflammatory and apoptosis signaling pathways without lowering heart rate, where the preclinical studies used a neural stimulator prototype to deliver VST that non-selectively stimulates both afferent axons and efferent axons in the vagus nerve according to a predetermined schedule for the VST (e.g. Hamann et al., Vagus nerve stimulation improves left ventricular function in a canine model of chronic heart failure, *Eur Journal Heart Fail* 2013; 15:1319-1326). ANS may be delivered non-selectively to afferent and efferent axons at low levels to avoid or inhibit bradycardia responses induced by stimulation of the vagus nerve. ANS may be delivered with a low ANS intensity that is therapeutically effective for the cardiovascular disease and that does not significantly drive a lower intrinsic heart rate. Heart rate may be maintained during ANS without resort to bradycardia support pacing of the myocardium during ANS. ANS may be delivered with a therapeutically-effective dose to achieve its beneficial effects on autonomic function without significant chronotropic side effects from acutely-observable and significant heart rate drops (e.g. 5% mean heart rate drop or more), improving the tolerability. For example, an ANS dose (e.g. a dose of vagal stimulation) may have a, intensity that causes a subtle, inconsistent response that is detectable using statistical measures such as a T-score or Z-score, as discussed in more detail below.

Furthermore, it has been observed that the evoked response to low level vagal stimulation is dependent on the background sympathetic activity of the patient. As will be discussed in more detail below, various embodiments may use low level ANS doses induce evoked responses that may be used as a surrogate for monitoring the background autonomic activity. Thus, a brief discussion of low-level ANS is provided below using vagal nerve stimulation (VNS) as an example. Given the complexity of the ANS and interrelation with many physiological functions, these subtle, inconsistent responses are not detectable simply by observing an acute heart rate or blood pressure response. Rather, the subtle, inconsistent responses to the dose of neural stimulation may be detected using statistical techniques to provide an evoked response metric (ERM) such as a T-score or Z-score. These subtle, inconsistent physiological responses to the dose of neural stimulation may have a dependence on the background autonomic activity of the patient, and thus may be used to monitor, by way of example, therapy effectiveness, patient-compliance, disease progression and cardiac contractility modulation.

The vagus nerve is a complex physiological structure with many neural pathways that are recruited at different stimulation thresholds. Various physiological responses to VNS are associated with various VNS doses. For example, FIG. 1 illustrates increasing VNS intensity from the left side to the right side of the figure, and further illustrates intensity thresholds that elicit various physiological responses to VNS. VNS causes a physiological response "A" at a lower intensity than an intensity at which VNS causes a physiological response "B", which occurs at a lower VNS intensity than an intensity at which VNS causes a physiological response "C". Stated another way, VNS has to reach a certain level before triggering response "A," and has to reach higher levels to trigger responses "B" and "C".

The physiological responses at the lower VNS intensities may have therapeutically-effective results for cardiovascular diseases such as HF. These intensities may be used to deliver a therapy (VST). These responses mediate or provide pathways for these therapies. Examples of such responses that are beneficial for HF at the lower VNS intensities include anti-inflammation, anti-sympathetic, and anti-apoptosis responses, and an increased NO. The physiological responses at the higher VNS intensities may not be desirable. Examples of responses to higher VNS intensities that may reduce the ability of the patient to tolerate VNS include, but are not limited to, reduced heart rate, prolonged AV conduction, vasodilation, and coughing. Not only may the physiological responses at the lower VNS intensities be therapeutic, the responses are dependent on the background autonomic activity and may be used as a surrogate for the autonomic health of the patient.

The intensity of the VNS can be adjusted by adjusting parameter(s) of the stimulation signal. Generally, dose may be changed by changing the amount of charge delivered over a period of time. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal, a stimulation burst frequency, a pulse width, a pulse duty cycle and/or a burst duty cycle.

Figure 2:
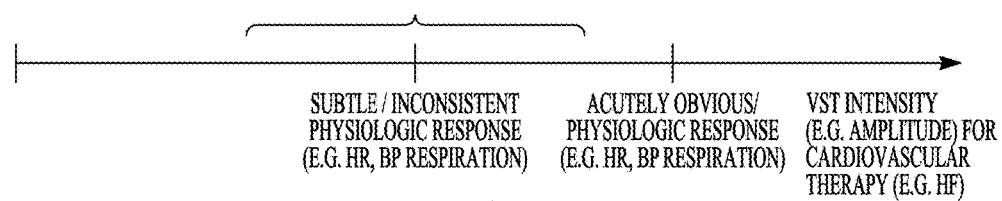
FIG. 2 illustrates increasing VNS intensity from the left side to the right side of the figure and a subtle, inconsistent physiologic response (e.g. a subtle, inconsistent change in heart rate, blood pressure and/or respiration) for the VNS, and further illustrates an intensity threshold that elicits an acutely-observable and significant (e.g. 5% reduction or more) reduced heart rate response to VNS.

FIG. 2 illustrates increasing VNS intensity from the left side to the right side of the figure and a subtle, inconsistent physiologic response (e.g. a subtle, inconsistent change in heart rate, blood pressure and/or respiration) for the VNS, and further illustrates an intensity threshold that elicits an acutely-observable and significant (e.g. 5% reduction or more) reduced heart rate response to VNS. The subtle, inconsistent response may occur over a range in which the response is present in a smaller percentage of time (e.g. less consistent) toward the left side of the figure and the response is present in a larger percentage of time (e.g. more consistent) toward the right side of the figure. Similarly, the responses may be smaller toward the left side of the figure and large toward the rights side of the figure. Larger periods of time may be used to detect the subtle, inconsistent responses toward the left side of the figure and shorter periods of time may be used to detect the larger and/or more consistent responses toward the right side of the figure. Techniques described herein may be used to detect the subtle and/or inconsistent physiological response and/or detect non-subtle effects that are intermittent and not seen with acute testing. As described herein, these techniques may be used to monitor autonomic health by delivering a VNS dose and detecting the subtle and/or inconsistent physiological responses caused by the dose, which provide an indication of the background autonomic activity.

Some embodiments may include a system for delivery a therapy (e.g. VST). For an open loop VST system, physiologic parameter(s) may be monitored during VST testing.

This VST testing may be based on a relatively large human population to determine the heart rate threshold. The VST testing may also be performed specifically for a patient during the implantation procedure using a process that verifies capture of the vagus nerve using observed heart rate reduction, that determines the intensity threshold at which the heart rate reduction is observed, and that uses the intensity threshold to provide and set the VST intensity below the heart rate threshold that causes the acutely observable and obvious heart rate reduction. The subtle, inconsistent response found at lower intensities may have a heart rate effect, but the heart rate effect is a subtle effect that is not an acutely-observable and significant drop in heart rate. For example, vagal stimulation pulses of a first amplitude may capture some nerve fibers in the cervical vagus nerve to cause the subtle heart rate effect, and vagal stimulation pulses of a second, higher, amplitude may capture addition nerve fibers in the cervical vagus nerve to cause the acutely-observable and significant drop in heart rate. It is believed that effective cardiovascular therapy, such as heart failure (HF) therapy, may be titrated to provide a targeted subtle, inconsistent physiologic response.

Figure 3:
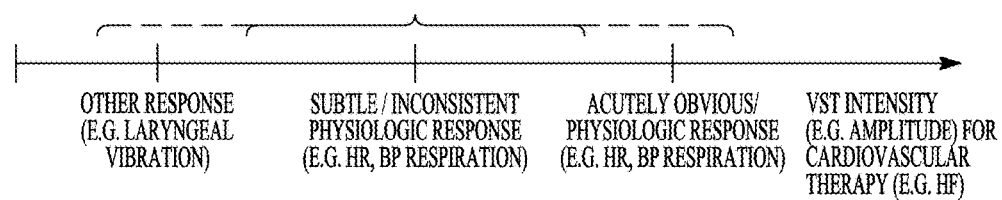
FIG. 3 illustrates increasing VNS intensity from the left side to the right side of the figure and a subtle and/or inconsistent physiologic response (e.g. a subtle change in heart rate, blood pressure and/or respiration) for the VNS, and further illustrates an intensity threshold that elicits an acutely-observable physiological response such as an acutely-observable and significant reduced heart rate response to VNS and another intensity threshold that elicits another physiological response (e.g. laryngeal vibration) to VNS.

FIG. 3 illustrates increasing VNS intensity from the left side to the right side of the figure and a subtle and/or inconsistent physiologic response (e.g. a subtle change in heart rate, blood pressure and/or respiration) for the VNS, and further illustrates an intensity threshold that elicits an acutely-observable physiological response such as an acutely-observable and significant reduced heart rate response to VNS and another intensity threshold that elicits another physiological response (e.g. laryngeal vibration) to VNS. Preclinical studies indicate that laryngeal vibration is detected at a lower VNS intensity threshold than the VNS intensity threshold for eliciting the acutely observable heart rate response. In some embodiments, the intensity threshold that causes the acutely-observable and significant reduced heart rate response may function as an upper boundary for allowable adjustments to the intensity to find the sweet spot, or may be used with a positive or negative offset to identify upper boundary for allowable adjustments. In some embodiments, the intensity threshold that causes the laryngeal vibrations may function as lower boundary for allowable adjustments to the intensity to find the sweet spot, or may be used with a positive or negative offset to identify lower boundary for allowable adjustments. FIG. 3 illustrates, by way of example, a candidate dose range that may extend through a range of intensities.

In embodiments in which VNS is delivered for a therapy, the therapeutic efficacy of the VST can be assessed acutely (e.g. within seconds or minutes) such as may be beneficial for a closed loop system or during an implantation procedure, and can be assessed on a longer term basis (e.g. on the order of hours, days, weeks, and months) such as may be beneficial to provide follow-programming updates for either open loop or closed loop systems. Examples of acute markers which could be measured to tell if the dose is in the therapeutic effective range include anti-inflammatory cytokines and autonomic balance markers. Examples of anti-inflammatory cytokines include serum TNF-alpha, IL-1, IL6, etc. Examples of autonomic balance markers include plasma NE (an indicator of sympathetic tone), heart rate variability (HRV) and heart rate turbulence (HRT). Longer term assessment of therapeutic efficacy can be determined using various methods currently used to monitor the progression of heart failure (e.g. electrogram readings and various measures of cardiac output, contractility, and size of the left ventricle). Other physiological responses that in and of themselves are not beneficial for the therapy, such as laryngeal vibration, may be used if their response threshold has a known relationship to trigger desired mediators (e.g. mediators, anti-apoptosis mediator, and anti-sympathetic) through which the applied VST provides effective therapy for the cardiovascular disease.

Various embodiments of the present subject matter may monitor an evoked response of neural stimulation for a desirable subtle and/or inconsistent response that may be detected using statistical analysis (e.g. T-score or Z-score). This subtle and/or inconsistent response may be used to monitor autonomic health. This subtle and/or inconsistent response may be used to monitor autonomic health may be used to control or evaluate a therapy. An evoked response may be illustrated using intermittent neural stimulation as discussed below.

Figure 4:
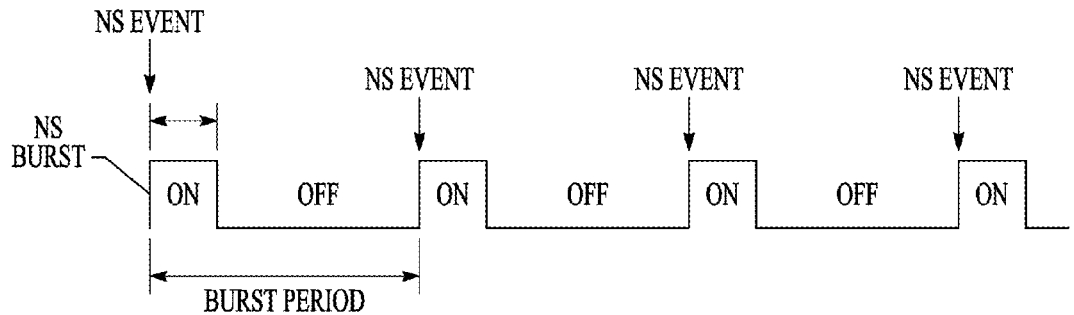
FIG. 4 illustrates a train of neural stimulation bursts (e.g. parasympathetic stimulation bursts). The train of neural stimulation bursts may be referred to as intermittent neural stimulation (INS).

FIG. 4 illustrates a train of neural stimulation bursts (e.g. parasympathetic stimulation bursts). The train of neural stimulation bursts may be referred to as intermittent neural stimulation (INS). The time-course of neural stimulation may alternate between intervals of stimulation being ON when pulse(s) are delivered and stimulation being OFF when no pulses are delivered. Each burst includes a plurality of pulses (not illustrated) within the burst. The duration of the stimulation ON interval is sometimes referred to as the stimulation duration or burst duration. The start of a stimulation ON interval is a temporal reference point NS Event. The time interval between successive NS Events is the INS Interval, which is sometimes referred to as the stimulation period or burst period. For an application of neural stimulation to be intermittent, the stimulation duration (i.e., ON interval) must be less than the stimulation period (i.e., INS Interval) when the neural stimulation is being applied. The duration of the OFF intervals of INS are controlled by the durations of the ON interval and the INS Interval. The duration of the ON interval relative to the INS Interval (e.g., expressed as a ratio) is sometimes referred to as the duty cycle of the INS. In the illustration, each burst has an equal duration (e.g. on the order of 10 seconds) and the bursts are separated by a burst period (e.g. on the order of one minute). The duration and/or burst period may be adjusted during the therapy to adjust the therapy dose and the evoked response. The dose and evoked response may be adjusted by changing the amplitude, pulse frequency, and/or pulse width of the neural stimulation pulses within the burst.

Figure 5A:
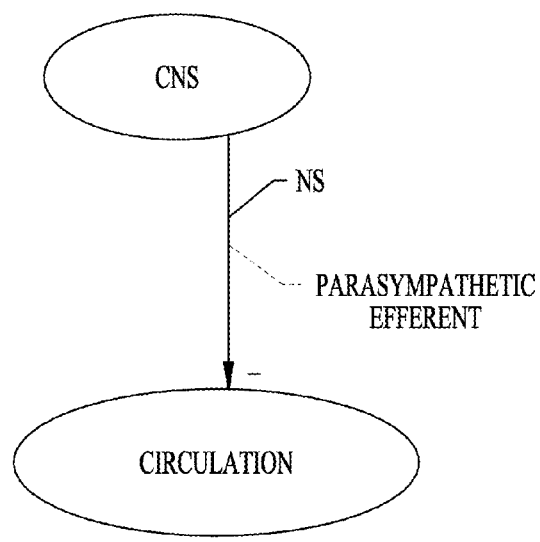
FIG. 5A illustrates an efferent parasympathetic target.
Figure 5B:
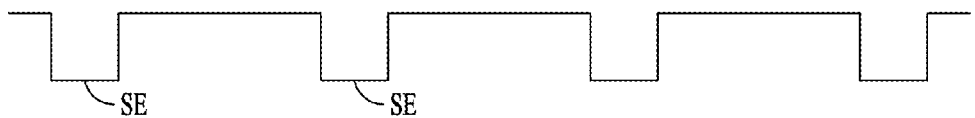
FIG. 5B illustrates a direct response on circulation (e.g. lowered heart rate or blood pressure) to the parasympathetic stimulation pulse train, as illustrated in FIG. 4, at an efferent parasympathetic target, as illustrated in FIG. 5A.
Figure 6A:
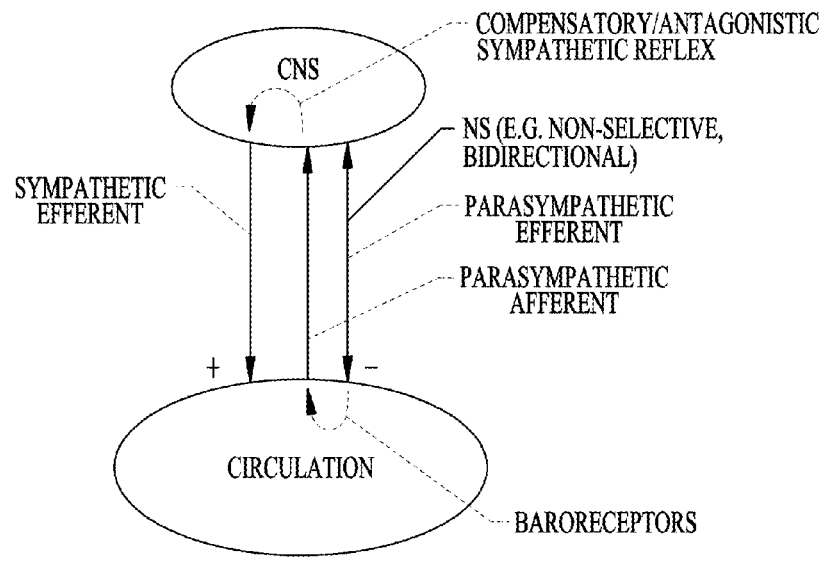
FIGS. 6A and 6B illustrate efferent and afferent parasympathetic stimulation with an afferent parasympathetic pathway carrying signals to the CNS and an efferent sympathetic pathway from the CNS carrying reflex stimulation to the target.
Figure 6B:
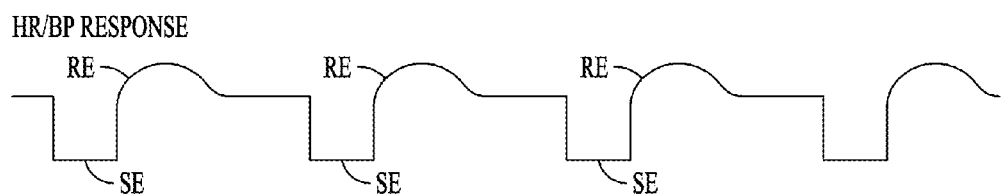

FIGS. 5A, 5B, 6A and 6B illustrate applications of the neural stimulation illustrated in FIG. 4 to a target to elicit an ANS effect on heart rate (HR) or blood pressure (BP). It is noted that the ANS also has an effect on respiration. Negative-going waveforms illustrated in FIGS. 5B and 6B indicate a decrease in HR or BP, such as expected from parasympathetic stimulation, while positive-going waveforms indicate an increase in HR or BP, such as expected from sympathetic stimulation. FIGS. 5A and 5B illustrate stimulation parameters adjusted to elicit a direct parasympathetic effect. FIGS. 6A and 6B illustrate stimulation parameters adjusted to elicit direct parasympathetic and reflex sympathetic effects.

FIG. 5A illustrates an efferent parasympathetic target, and FIG. 5B illustrates a direct response on circulation (e.g. lowered heart rate or blood pressure) to the parasympathetic stimulation pulse train, as illustrated in FIG. 4, at an efferent parasympathetic target, as illustrated in FIG. 5A. Action potentials in afferent nerves travel toward the central nervous system (CNS), and action potentials in efferent nerves travel away from the CNS. As illustrated in FIG. 5B, the direct response referred to herein as a stimulation effect (SE)

attributed to the selective stimulation of the efferent pathway follows the time course of neural stimulation pulses and returns to baseline between stimulation bursts. The efferent stimulation in this example results in a small direct response in HR or BP that does not elicit a measurable reflex response, as indicated by immediate return to baseline of the response following termination of the stimulation burst.

FIGS. 6A and 6B illustrate efferent and afferent parasympathetic stimulation with an afferent parasympathetic pathway carrying signals to the CNS and an efferent sympathetic pathway from the CNS carrying reflex stimulation to the target. FIG. 6B illustrates a direct and reflex response of the circulation (e.g., heart rate decrease then increase or blood pressure decrease then increase) to the parasympathetic stimulation pulse train, as illustrated in FIG. 4, at an efferent parasympathetic target as illustrated in FIG. 6A. As illustrated in FIG. 6B, the stimulation of the efferent pathway provides a direct response referred to herein as a stimulation effect (SE) and a reflex response referred to herein as a reflex effect (RE). In this example, the efferent stimulation elicits a reflex effect when baroreceptors in FIG. 6A respond to the lowered HR or BP, sending impulses to the CNS in the afferent nerve illustrated in FIG. 6A and thereby eliciting a compensatory sympathetic reflex, which may also be referred to as an antagonistic sympathetic reflex, that increases HR and BP via impulses conveyed from the CNS in the sympathetic efferent pathway illustrated in FIG. 6A. As illustrated in FIG. 6B, the stimulation effect ends quickly after the end of the stimulation burst, whereas the reflex effect continues measurably after the end of the stimulation burst. It is noted that the reflex response is a complex reaction that may have other contributing factors such as chemoreceptor activity. Furthermore, the stimulation may be a non-selective, bidirectional stimulation that elicits action potentials in the parasympathetic nerve both in the afferent direction toward the CNS as well as in the efferent direction. The elicited action potentials in the afferent direction toward the CNS also affect the evoked response. The present subject matter is not limited to a particular mechanism.

Figure 7A:
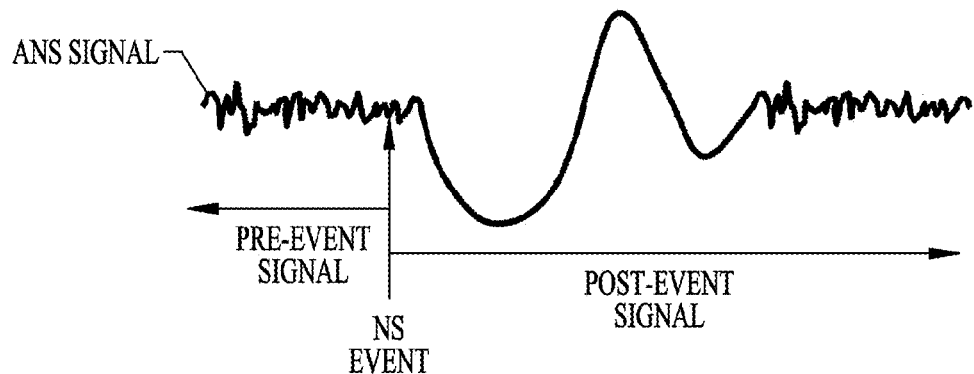
FIGS. 7A-7B illustrate various embodiments for monitoring a response to an intermittent NS burst.
Figure 7B:
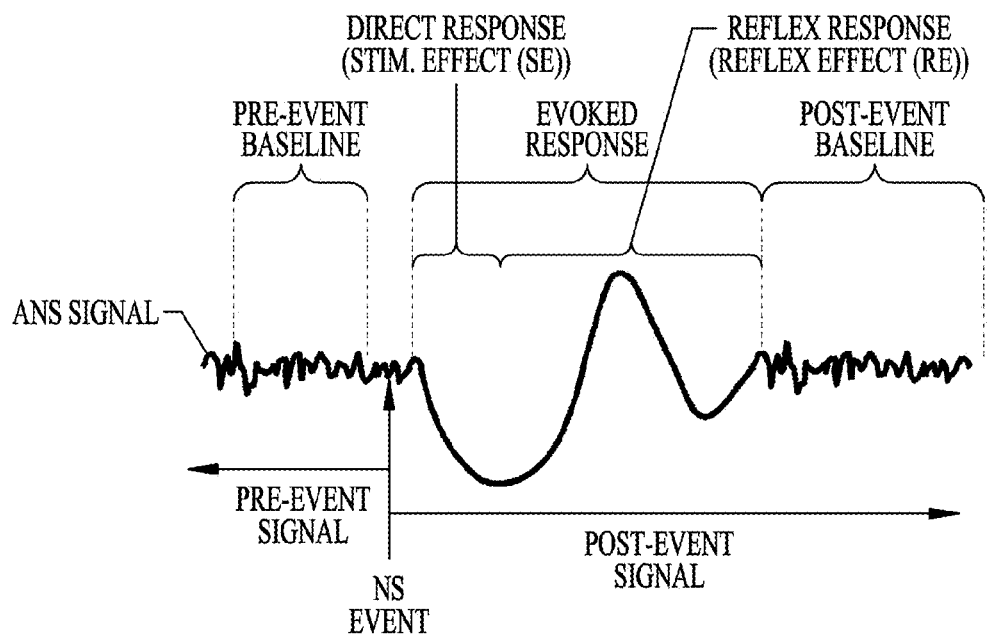

FIGS. 7A-7B illustrate various embodiments for monitoring a response to an intermittent NS burst. Multiple bursts can be analyzed, according to various embodiments. Each figure illustrates one neural stimulation burst among a plurality of INS stimulation bursts of a programmed NS therapy. The NS burst includes a plurality of NS pulses that are preceded and followed by a time without NS pulses. In one embodiment illustrated in FIG. 7A, an ANS signal may be monitored over time and marked with the NS event, which is a time point with a fixed offset from the start of the NS burst. The NS event offset from the NS burst start may be a zero offset, a negative offset, or a positive offset depending on various signal analysis embodiments. The NS event may divide the ANS signal into a Pre-Event Signal and a Post-Event Signal. As illustrated in FIG. 7B, the pre-event signal may contain a pre-event baseline and the post-event signal may contain an evoked response and a post-event baseline. The evoked response may include a direct response (stimulation effect (SE)) and a reflex response (reflex effect (RE)).

As identified previously, the subtle and/or inconsistent response may be used to monitor autonomic health. The autonomic nervous system influences, among other things, the performance of the heart. The accelerative effects of the sympathetic nervous system on heart rate are dependent on the background level of vagal activity. For example, sympathetic heart rate effects are substantially smaller with high levels of vagal tone than with low vagal background activity, and vagal effects are progressively stronger with increasing sympathetic background activity. Each of the two autonomic divisions can both inhibit and enhance the activity of the other via effects on the release of neurotransmitters at the synaptic junctions. The inhibition of the cardiac effects from sympathetic nerve stimulation by the presence of background vagus nerve stimulation has been described using the term "accentuated antagonism."

Embodiments of the present subject matter may monitor an evoked response to an ANS dose to monitor background autonomic activity. The reflex effect (RE) of an evoked response to an ANS dose is opposite to the stimulation effect (SE) to the ANS dose. For example, an elevated sympathetic activity in the background will be more sensitive to a sympathetic response effect to parasympathetic stimulation. More sympathetic neurotransmitters at the synaptic junctions may make the sympathetic response effect more detectable by being more consistently present and/or by being a greater response when present.

Figure 8A:
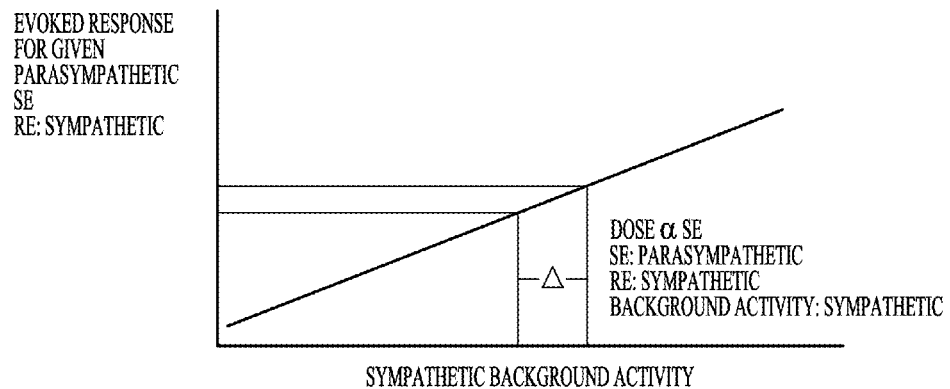
FIGS. 8A-8B provides simple illustrations of how the background autonomic activity may cause changes in an evoked response.
Figure 8B:
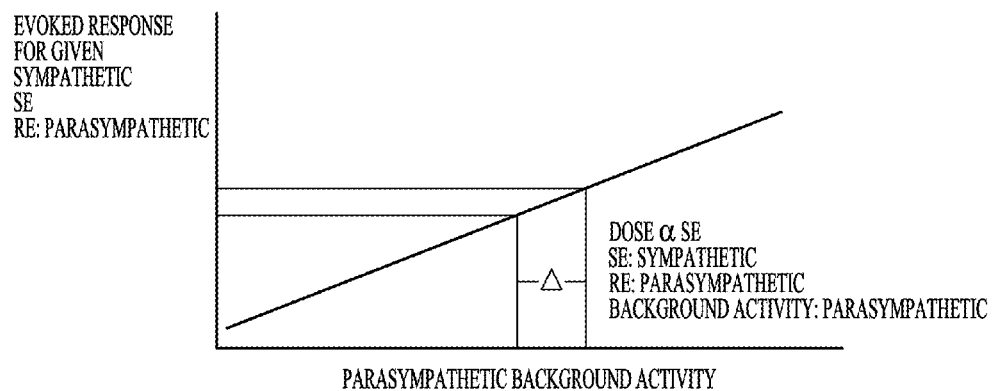

FIGS. 8A-8B provides simple illustrations of how the background autonomic activity may cause changes in an evoked response. The figure simply illustrates a function between the background activity and evoked response as a linear function to illustrate that larger background activity corresponds to larger evoked responses. This function may not be linear. However, these figures illustrate the general concept that more sympathetic neurotransmitters at the synaptic junctions may make the sympathetic response effect more detectable by being more consistently present and/or by being a greater response when present, and more parasympathetic neurotransmitters at the synaptic junctions may make parasympathetic response effect more detectable by being more consistently present and/or by being a greater response when present.

For example, FIG. 8A provides a simple illustration of a sympathetic evoked response for a given parasympathetic dose, where the evoked response varies based on sympathetic background activity according to a function which is simply illustrated as a linear function. Similarly, FIG. 8B provides a simple illustration of a parasympathetic evoked response for a given sympathetic dose, where the evoked response varies based on parasympathetic background activity according to a function which is simply illustrated as a linear function. The dose affects the SE. In each of these illustrations, a change in the reflex effect (RE) for a given dose may indicate a change (Δ) in the background activity. Where the background activity has the same tone (e.g. parasympathetic or sympathetic) as the RE as illustrated in both FIGS. 8A and 8B, then an observed increase in the RE corresponds to an increase in the background tone. Where the background activity and the RE have different tone, then an observed increase in the RE corresponds to a decrease in the background tone.

Figure 9:
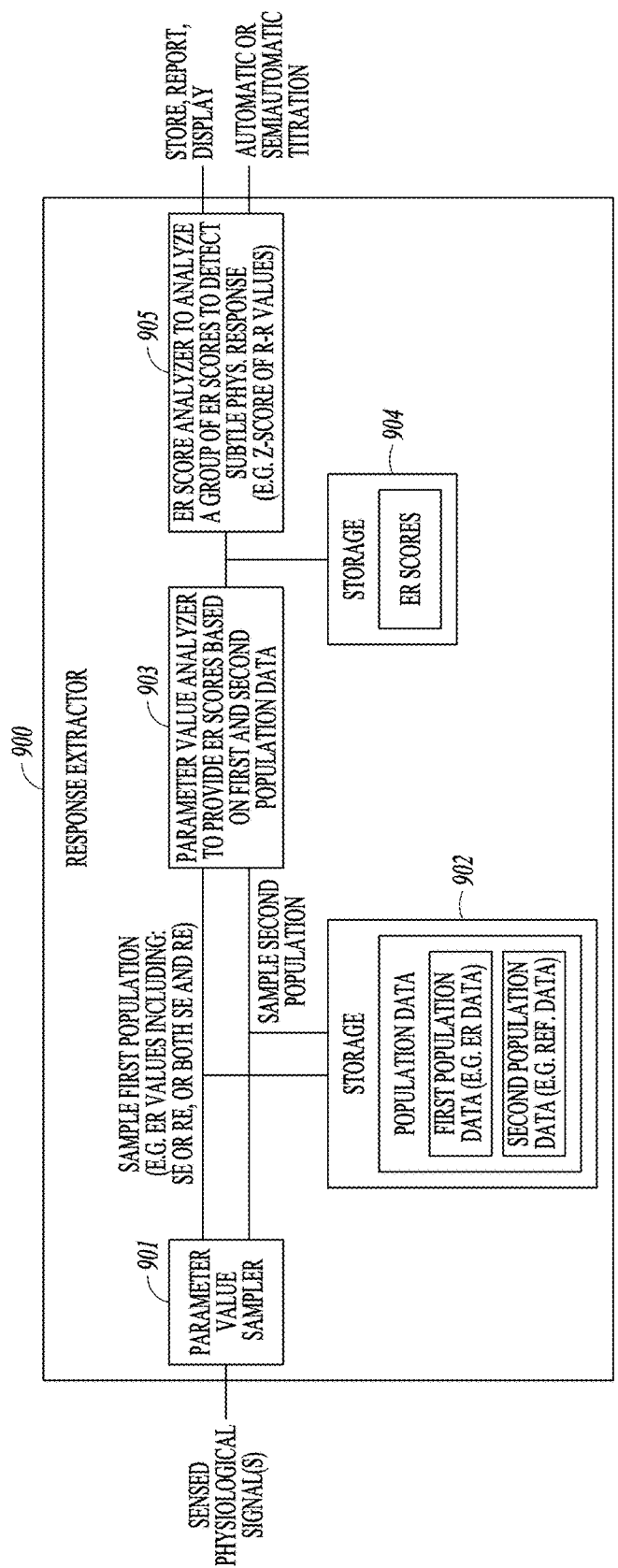
FIG. 9 illustrates, by way of example and not limitation, an embodiment of a response extractor configured for use to analyze an evoked response to detect subtle, inconsistent changes in the evoked response.

FIG. 9 illustrates, by way of example and not limitation, an embodiment of a response extractor 900 configured for use to analyze an evoked response to detect subtle, inconsistent changes in the evoked response. The response extractor may be implanted within the patient or be external to the patient. The response extractor may be used in a system that stores and reports data from the response extractor for use in monitoring autonomic health. In some embodiments, by way of example, the response extractor may be used in a system that performs an automatic or semiautomatic titration of ANS therapy.

The response extractor 900 may include a parameter value sampler 901 configured to receive sensed physiological signal(s) from physiological sensor(s) used to sense evoked response(s) to ANS. Examples of such sensors include heart rate sensors, respiration sensors, blood pressure sensor, and electrocardiogram sensors. The parameter value sampler 901 may, by way of example, be used to detect R-R interval values for sample(s) of the physiological signal(s). The parameter value sampler 901 may derive other values such as rate variability values (e.g. heart rate variability (HRV) or respiratory rate variability (RRV)) for use in detecting the subtle, inconsistent physiologic response. Various embodiments may monitor changes in contractility, such as may be used to monitor Cardiac Contractility Modulation (CCM). CCM applied with a regular ON/OFF cycle may be detected if CCM changes contraction intensity or rate either directly or through a neuro mechanism.

Some embodiments may monitor patient condition and/or time The data may from the physiological sensor(s) be tagged with the patient conditions or activity or time. The data from the physiological sensor(s) may be stored with the tagged condition or tagged time. This information may be trended or otherwise analyzed to provide additional insight into the evoked response and autonomic health. Furthermore, this information may be used to allow a clinician, or patient or other caregiver, to adjust therapy. Some system embodiments may configured to provide automatic or semi-automatic therapy adjustments based on this information. By way of example, a semi-automatic therapy adjustment may automatically propose therapy parameters that can be adjusted by a clinician before implementing, or that can be implemented by a clinician without adjustment.

The parameter value sensor may sample values from the sensed physiological signal(s). If the signal(s) are digital, the sampler may extract all digital values or a representative sampling of the signals that still provides the desired resolution. The sample time may but need not correspond to the burst interval of an intermittent neural stimulation. Some embodiments may only sample during a window of time. The sample time may be a sample (e.g. ER sample or NE sample) within window(s) of time controlled by NS events (e.g. beginning of a train of bursts in an intermittent neural stimulation therapy). The sample of ER values may include a sample of SE values, a sample of RE values, or both a sample of SE values and a sample of RE values. The reference values may include NE values, or NE values and ER values. For example, an NS event may identify the beginning of burst of neural stimulation pulses. This may be used to trigger sensing for a period of time during which the signal(s) are expected to show a direct effect and reflex effect. For example, if a 10 second burst of stimulation is provided, the window may be about 15 to 25 seconds to capture the direct effect (about 10 seconds) and reflex effect (additional 5-15 seconds after the direct effect).

The values from the parameter value sampler 901 may be stored in a storage 902. The storage 902 may be memory in an internal or external device. Further the storage may be local or remote to the parameter value sampler. The values may be stored without distinguishing between the first and second populations, and then later processed to extract the first and second population data. In some embodiments, the parameter value sampler distinguishes between the first population and the second population, and the storage distinguishes between the first population data and the second population data. The first population data may include, among other types of data, evoked response (ER) values corresponding to the evoked physiological responses. The second population data may include, among other types of data, may include reference values that include no effect (NE) values corresponding to times without an evoked physiological response.

The response extractor 900 may include a parameter value analyzer 903 to provide ER scores based on the first and second population data. The ER scores quantify a relationship between the first population data and the second population data, and may use statistical analysis to quantify the relationship. The relationship may be converted to a standard score, such as may promote further analysis to detect subtle and/or inconsistent physiological responses. For example, the parameter value analyzer may be configured to quantify a statistical difference between the ER values and the reference values. The response extractor 900 may include a storage to store the ER scores 904. The storage 904 may be memory in an internal or external device. Further the storage may be local or remote to the parameter value sampler. The storage 904 may be separate with respect to or may be integrated with storage 902.

The response extractor 900 may include an ER score analyzer 905 to analyze a group of ER scores to detect subtle, inconsistent responses. In some embodiments, the response extractor 900 may communicate information for use to store, report, display ER scores and other data useful for consideration by a clinician or other caregiver or patient to titrate the stimulation. In some embodiments, the response extractor may communication information for use in automatically or semiautomatically titrate the stimulation. "Semiautomatic" indicates that some processes are automatically performed, and others are triggered or manually performed. Thus, an example of a semiautomatic process may involve automatically providing a suggested change for titrating the stimulation, and then implementing the change in response to a manually-provided confirmation from the user.

The response extractor may be contained within a single device (e.g. external device or internal device), or may be distributed into two or more devices (e.g. two or more of internal device(s), external device(s), network device(s)).

Figure 10:
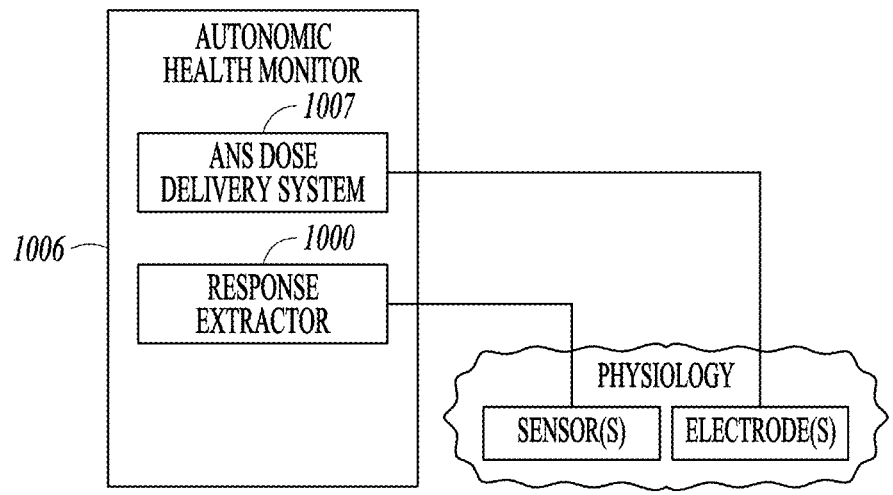
FIG. 10 illustrates an example of a system that includes an autonomic health monitor.

FIG. 10 illustrates an example of a system that includes an autonomic health monitor. The illustrated autonomic health monitor 1006 may include an ANS dose delivery system 1007 configured to deliver electrical pulses to an autonomic target for an ANS dose, and may further include a response extractor 1000, which may be the same or similar to the response extractor 900 in FIG. 9. The ANS dose delivery system 1007 delivers the dose to the physiology in order produce the response that is to be extracted by the response extractor 1000. The dose may be delivered to through electrodes, and the response may be detected using sensor(s). Such a monitor may be implantable or external to the patient.

Figure 11:
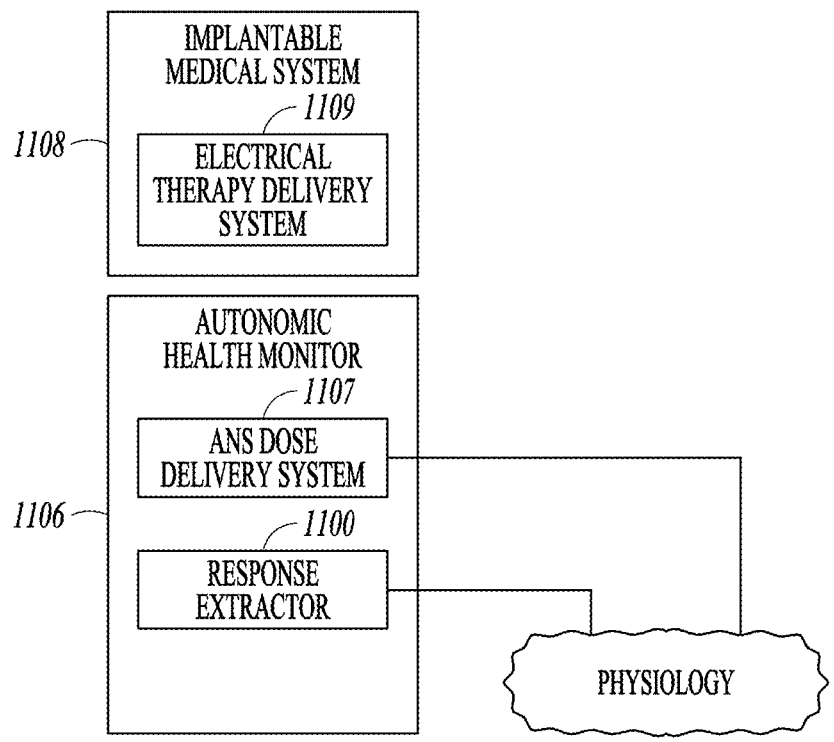
FIG. 11 illustrates an example of a system that includes an implantable medical system and an autonomic health monitor.

FIG. 11 illustrates an example of a system that includes an implantable medical system 1108 and an autonomic health monitor 1106. The implantable medical system 1108 may include an electrical therapy delivery system 1109 such as, by way of example and not limitation, a neurostimulator or a myocardial stimulator. The autonomic health monitor may include an ANS dose delivery system 1107 configured to deliver electrical pulses to an autonomic target for an ANS dose, and may further include a response extractor 1100. The ANS dose delivery system 1107 may be separate from the electrical therapy delivery system 1109. The dose may be delivered separately from any therapy delivered by the electrical therapy delivery system 1109. The autonomic health monitor 1106 may be an external device.

Figure 12:
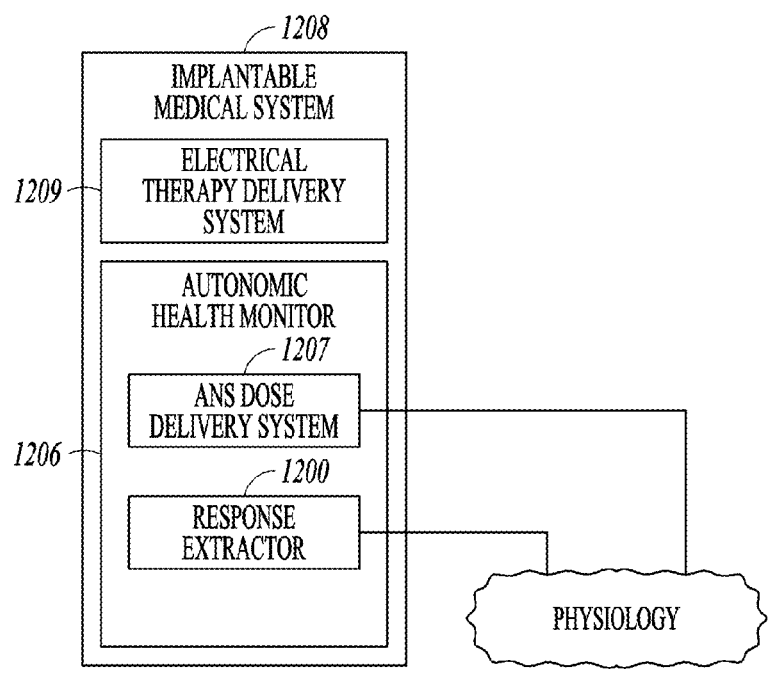
FIG. 12 illustrates an example of an implantable medical system that includes an electrical therapy delivery system and an autonomic health monitor.

FIG. 12 illustrates an example of an implantable medical system 1208 that includes an electrical therapy delivery system 1209 and an autonomic health monitor 1206. The electrical therapy delivery system 1209 may be, by way of example and not limitation, a neurostimulator or a myocardial stimulator. The autonomic health monitor may include an ANS dose delivery system 1207 configured to deliver electrical pulses to an autonomic target for an ANS dose, and may further include a response extractor 1200. The ANS dose delivery system 1207 may be separate from the electrical therapy delivery system 1209. The dose may be delivered separately from any therapy delivered by the electrical therapy delivery system 1209.

Figure 13:
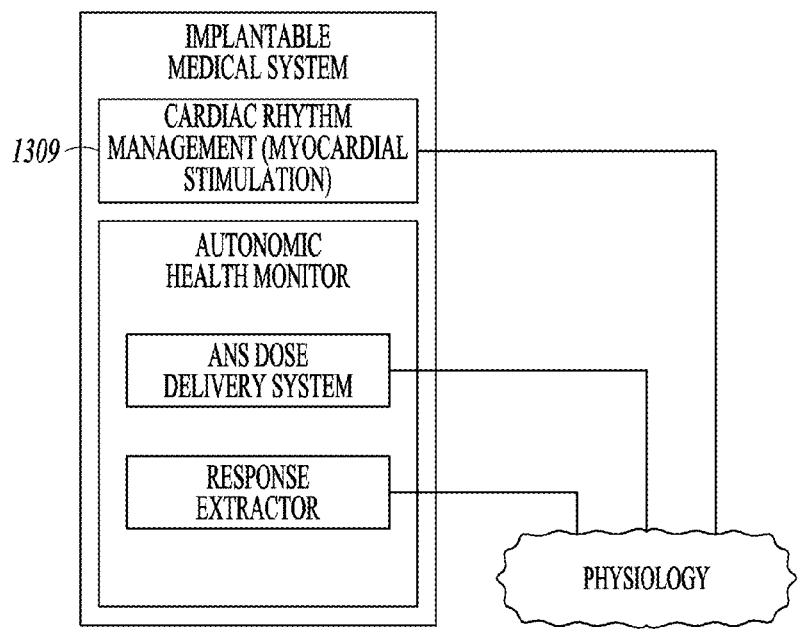
FIG. 13 illustrates an example of an implantable medical system, similar to the system illustrated in FIG. 12 that includes a cardiac rhythm management system and the autonomic health monitor.

FIG. 13 illustrates an example of an implantable medical system, similar to the system illustrated in FIG. 12 that includes a cardiac rhythm management system 1309 and the autonomic health monitor. The cardiac rhythm management system 1309 may configured to deliver myocardial stimulation as part of a bradycardia pacing therapy, anti-tachycardia pacing therapy, a cardiac resynchronization therapy (CRT), or a defibrillation or cardioversion therapy.

Figure 14:
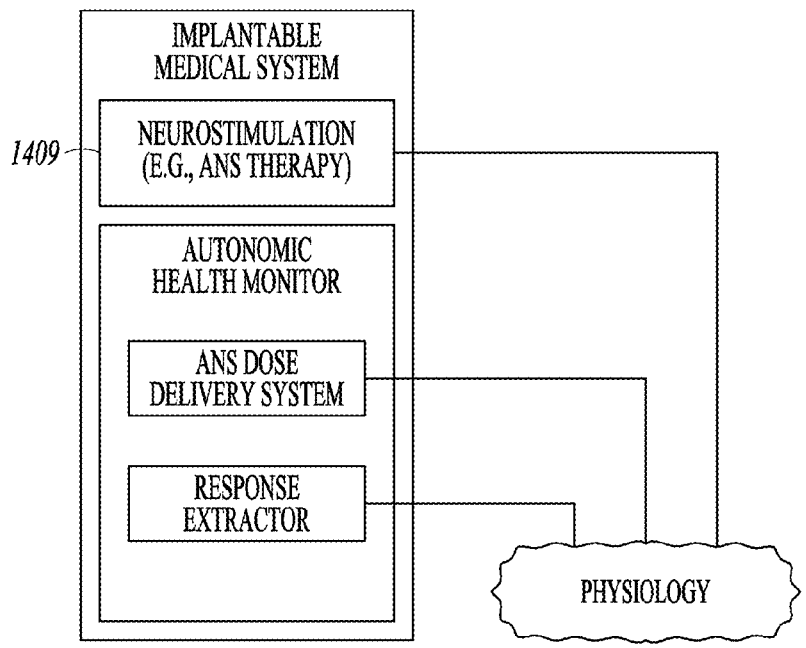
FIG. 14 illustrates an example of an implantable medical system similar to the system illustrated in FIG. 12 that includes a neurostimulation system and the autonomic health monitor.

FIG. 14 illustrates an example of an implantable medical system similar to the system illustrated in FIG. 12 that includes a neurostimulation system 1409 and the autonomic health monitor. The neurostimulation system 1409 may configured to deliver a neurostimulation therapy such as an ANS therapy. Examples of ANS therapies include, but are not limited to, heart failure and hypertension therapies. The neurostimulation may be delivered to a neural target such as, but not limited to, a vagus nerve, a carotid sinus nerve, a glossopharyngeal nerve, a baroreceptor region or a chemoreceptor region. Heart rate, by way of example, may be monitored using an electrode stub or electrodes on an implantable housing, or electrodes on or near the heart. The baroreceptor region, by way of example, may include carotid sinus baroreceptors or may include pulmonary artery baroreceptors.

Figure 15:
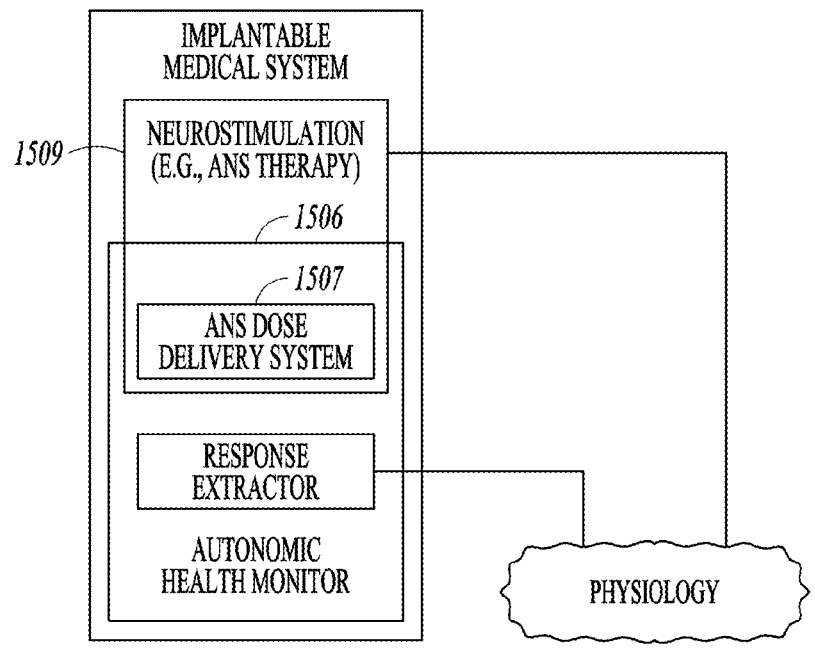
FIG. 15 illustrates an example of an implantable medical system that includes a neurostimulation system and the autonomic health monitor that share an ANS dose delivery system.

FIG. 15 illustrates an example of an implantable medical system that includes a neurostimulation system 1509 and the autonomic health monitor 1506 that share an ANS dose delivery system 1507. The ANS dose delivery system may be used to control the dose for the neurostimulation therapy. The ANS dose used to monitor the autonomic system may be the same dose as that used to deliver the neurostimulation therapy or may be a different dose.

Figure 16:
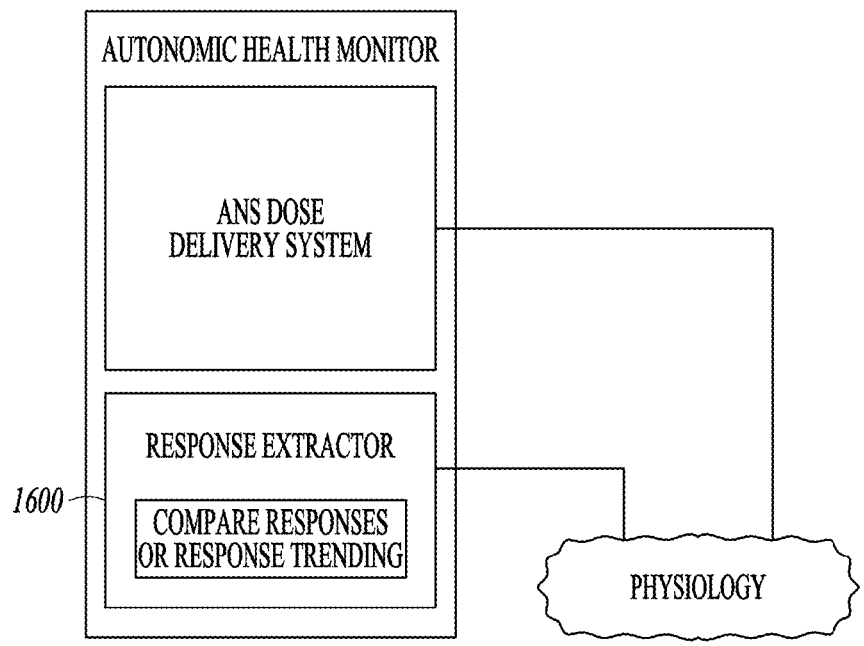
FIG. 16 illustrates an example of a system that includes an autonomic health monitor that uses a response extractor configured to compare responses to trend responses.
Figure 17:
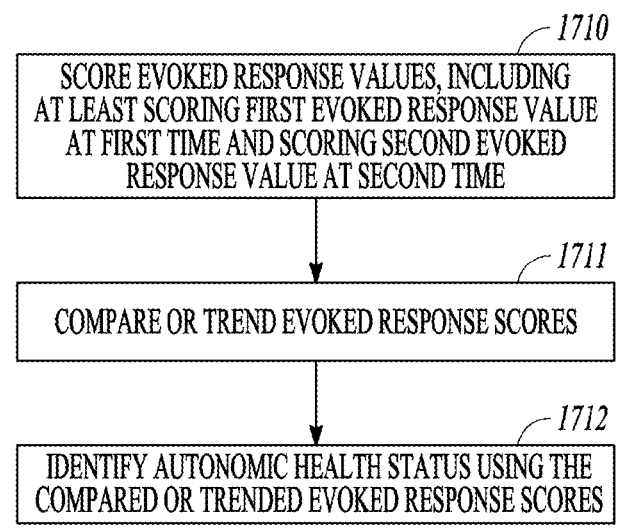
FIG. 17 illustrates an example of a method performed by the response extractor in FIG. 16.

FIG. 16 illustrates an example of a system that includes an autonomic health monitor that uses a response extractor 1600 configured to compare responses to trend responses. FIG. 17 illustrates an example of a method performed by the response extractor 1600 in FIG. 16. As represented at 1710, the response extractor may be used to score evoked response values including a first evoked response value at a first time and scoring a second evoked response value at a second time. As represented at 1711, he evoked response scores may be compared to a reference or to each other, or may be trended. The autonomic health status may be identified using the compared or trended evoked response scores, as represented at 1712.

Figure 18:
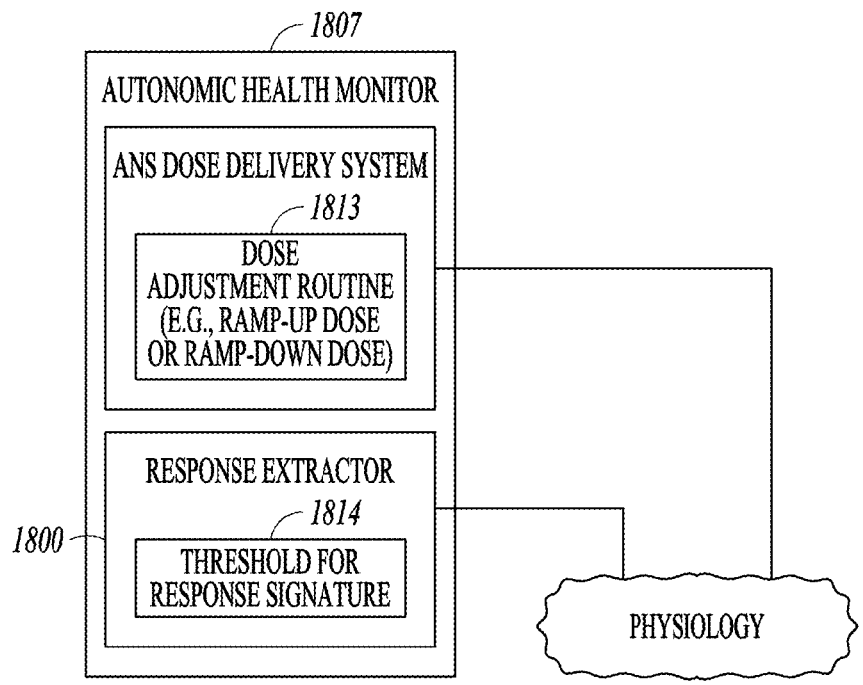
FIG. 18 illustrates an example of a system that includes an autonomic health monitor that includes an ANS dose delivery system with a dose adjustment routine, and that includes a response extractor to identify a response threshold.
Figure 19:
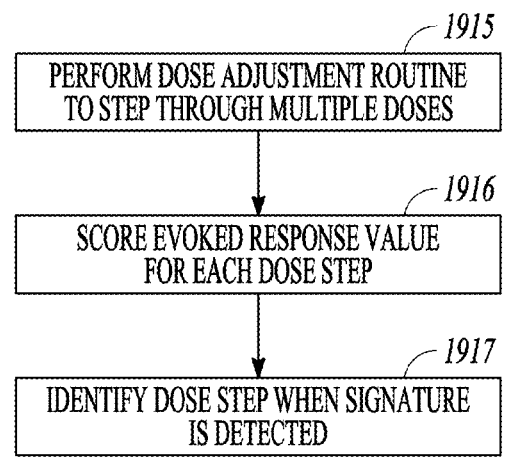
FIG. 19 illustrates an example of a method performed by the response extractor in FIG. 18.

FIG. 18 illustrates an example of a system that includes an autonomic health monitor that includes an ANS dose delivery system 1807 with a dose adjustment routine 1813, and that includes a response extractor 1800 to identify a response threshold 1814. The dose adjustment routine 1813 may be a programmed routine that steps through different dose or intensity steps (e.g. ramp up or ramp down). The response extractor 1800 is configured to identify the dose threshold where the response signature is first present. As identified with respect to FIG. 2, subtle, inconsistent responses toward the right side of the figure may be detected quicker than the subtle, inconsistent responses toward the left side of the figure. The amount of time to record data may depend on how subtle and inconsistent the responses are. Some embodiments may use different ANS doses with one dose to provide a quicker indicator of ANS response and another dose to provide a slower indicator of ANS response. FIG. 19 illustrates an example of a method performed by the response extractor 1800 in FIG. 18. At 1915, a dose adjustment routine is performed to step through multiple doses. An evoked response value is scored for each does step 1916, and the dose step is identified when the signature is detected 1917.

Figure 20A:
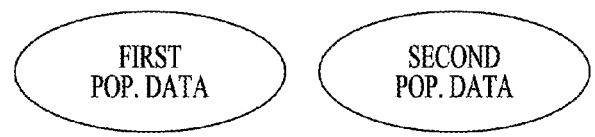
FIGS. 20A-20C illustrate some Venn diagrams for the first population data and the second population data.
Figure 20B:
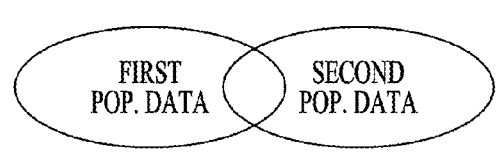
Figure 20C:
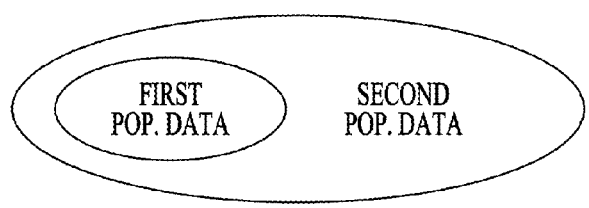

FIGS. 20A-20C illustrate some Venn diagrams for the first population data and the second population data. The first population data includes at least some ER values but may include other values as well. The second population data includes at least some NE values but may include other values as well. FIG. 20A illustrates that the first and second population data sets may be mutually exclusive. FIG. 20B illustrates that the first and second population data sets may include some data points that are in both the first and second population data. FIG. 20C illustrates that the second population data set is greater than and encompasses the entirety of the first population data. The first population data may include but is not limited to ER values, and the second population data may include but is not limited to NE values such that the second population data can function as reference values against which the first population data can be compared. Although the comparison may be made with more resolution if the first population data only includes ER values and the second population data only includes NE values, a meaningful comparison may be made even if the first population data includes some NE values and/or the second population data includes ER values.

Figure 21:
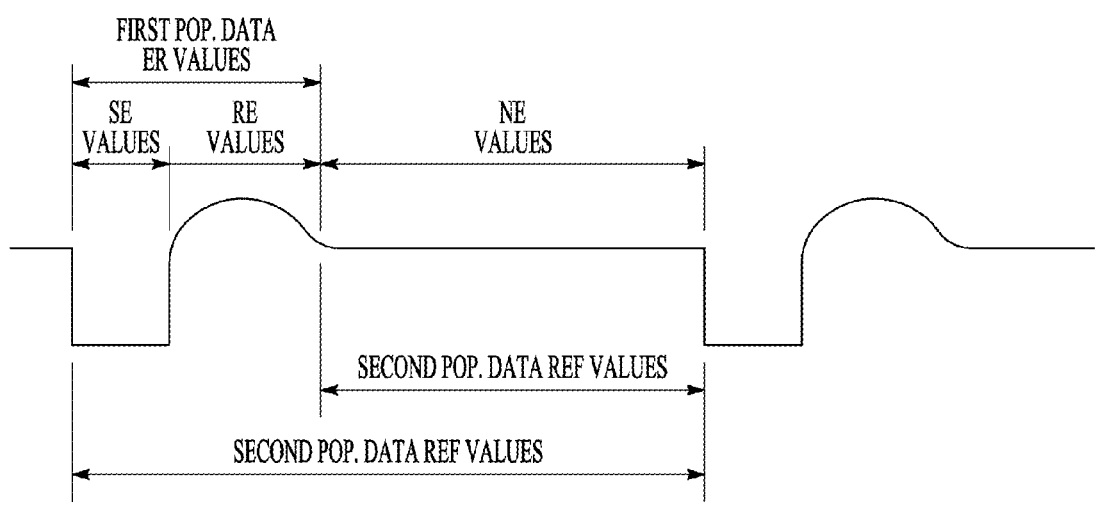
FIG. 21 illustrates an example of first population data and the second population data that may be extracted from a sensed physiological signal during intermittent neural stimulation.

FIG. 21 illustrates an example of first population data and the second population data that may be extracted from a sensed physiological signal during intermittent neural stimulation. The illustrated example of a response waveform is similar to the example of a waveform illustrated in FIG. 6B, and illustrates SE values, RE values, ER values where ER values include SE and RE values, and NE values. The first population data may include at least some SE values, or may include at least some RE values, or may include at least some SE and RE values. The second population data may include at least some NE values, or may include at least some NE values and some ER values. The population data may be but need not be contiguous data points from the sensed physiological signal. For example, the sensed signal may be sampled at different points during the period of the signal. In another example, a window may be defined for a portion of the period of the signal, and the sensed signal may be sampled within the window for one or more periods that may but need not be consecutive periods. In another example, the ANS therapy may be interrupted to provide a time within which to sense NE values. These interruption periods may be scheduled or triggered sufficiently often to maintain accurate reference values against which the ER values may be compared. In some embodiments, the neural stimulation may be intermittent neural stimulation and the reference values may be sampled to sense NE values between bursts of the intermittent neural stimulation.

The response extractor may use statistical techniques to quantify the evoked response value(s) against the reference values. For example, an individual evoked response value may be compared to reference values. The evoked response value may be a mean value of two or more evoked response values, and the reference values may be a mean value of reference values. The mean values may be a running average of a number of values to smooth out the quantified revoked response values. For example, the mean of values 1-5 may be determined, then the mean of values 2-6, and then the mean of values 3-7, etc. Again, these values may be from one or more periods of the sensed physiological signal.

Statistical techniques may be used to convert the measured responses into a standard form to describe measures within a distribution. Two examples of standardized forms are Z-scores and T-scores. Z-scores transform individual data points into a standard form, where the transformation is based on knowledge about the population's mean and standard deviation. Transforming raw scores to Z-scores does not change their distribution. T-scores transform individual data points in a sample of data points into a standard form where the conversion is made without knowledge of the population's mean and standard deviation. The scores are calculated using the mean and standard deviation of the sample as an estimate of the population's mean and standard deviation. By way of example, Z-scores may be used when the sample size is sufficiently large to provide a meaningful means and standard deviation calculations, and T-scores may be used for the smaller sample sizes. Thus, whether data points are scored using a Z-score or a T-score depends, among other things, on whether the data points represent the population or a sampling of the population which depends on whether the underlying data is considered to be the population or a sampling of the data.

Various embodiments may use statistical techniques to calculate an evoked response metric (ERM) to quantify the difference in a first population (with evoked response values) and a second population (with NE values). The statistical technique(s) may be used to detect responses that are subtle and/or inconsistent. A stronger response may be evident in a more consistent response. The first population may be taken from a first period of time and the second population may be taken during a second period of time. The ERM may be calculated as follows:

$$ERM = \frac{f(\text{First } Pop. \text{ Data}) - f(\text{Second } Pop. \text{ Data})}{V(\text{First and Second } Pop. \text{ Data})}$$

where f represents a function such as but not limited to mean, variance, maximum, minimum, $25^{th}$ percentile (P25), $75^{th}$ percentile (P75)), and where V represents a variability function (such as Standard Error or Standard Deviation). The first and second period of times may be mutually exclusive. The first period of time may be a subset of the second period of time. The first and second population data sets may be mutually exclusive or may include some data points that are in both the first and second population data. The second population data set may be greater than and encompass the entirety of the first population data. The first population data may include but is not limited to ER values, and the second population data may include but is not limited to NE values such that the second population data can function as reference values against which the first population data can be compared. The variability (V) of the first and second population data may be represented as a union of the first population data and the second population, such that data points found in both the first and second population data are present only one time in determining the variability so as not to provide extra weight to those data points found in both the first and second population data.

Using a 10 second ON 50 second OFF intermittent neural stimulation to provide a burst period of 60 seconds, by way of example and not limitation, some examples of ERM statistics that may be used include, but are not limited to, $ERM_1$, $ERM_2$ and $ERM_3$ as provided below.

$$ERM_1 = \frac{\text{Mean}(ER \text{ values 1 sec.per.}) - \text{Mean}(\text{values entire 60 sec.})}{\text{Standard Deviation}(\text{values during entire 60 sec.tr.per.})}$$

where the first population data is a sample of values within a 10 second stimulation ON window of time within the burst period, the second population data is the values throughout the burst period, and the variability is determined using values throughout the burst period. The function applied to the first population and the second population is a "mean" function, and the variability is a standard deviation of the values.

$$ERM_2 = \frac{\text{Mean}(ER \text{ values 10 sec.per.}) - \text{Mean}(\text{values remaining 50 sec.})}{\text{Standard Error}(\text{values during entire 60 sec.tr.per.})}$$

where the first population is the values during the stimulation ON portion, the second population data is the values during the stimulation OFF portion, and the variability is determined using values throughout the burst period. The function applied to the first population and the second population is a "mean" function, and the variability is a standard deviation of the values.

$$ERM_3 = \frac{P25(ER \text{ 10 sec.per.}) - P25(\text{values remaining 50 sec.tr.per.})}{\text{Standard Error}(\text{values during entire 60 sec.tr.per.})}$$

where the first population is the values during the stimulation ON portion, the second population data is the values during the stimulation OFF portion, and the variability is determined using values throughout the burst period. The function applied to the first population and the second population is a "P25 ($25^{th}$ percentile)" function, and the variability is a standard deviation of the values. $ERM_1$ is a Z-statistic and $ERM_2$ is a t-statistic. $ERM_3$ does not have a common name, but is an example of modifications that may be made to provide a useful metric for evaluating evoked response signatures. It is again noted that these are examples. For example, the first period is not necessarily limited to periods in which stimulation is present. ERM may be calculated at any time to determine if the beats under consideration are different from the beats around them or other reference beats. In a further example, an ERM may be calculated for each second in each trial, and not just during the duration of the stimulation burst (e.g. 10 second ON period of time).

The output from the response extractor may be used to determine a desirable pulse amplitude for the VST. A desirable pulse amplitude for a first VST may be used in a second VST. By way of example, a system may be configured to deliver neural stimulation using different therapy modes to sense values that may be used to detect a subtle physiologic response. For example, the first therapy mode may deliver 1 or more pulses times to every cardiac cycle, and the second therapy mode may deliver intermittent neural stimulation with scheduled burst times. For example, the first therapy mode (e.g. a pulse or pulses every cardiac cycle) may be delivered, and then the system may be switched to a second therapy mode (e.g. intermittent neural stimulation where each burst is longer than a cardiac cycle and successive bursts are separated by a time without stimulation that is also longer than a cardiac cycle). The NE values may be sensed to provide reference values during a time or times between neural stimulation bursts in the second therapy mode, and the ER values may be sensed during one or more bursts. The pulse amplitude that causes a desired subtle response during the second therapy mode, as determined using the ER values and the reference values, may be identified and used to as the pulse amplitude during the first therapy mode.

Figure 22:
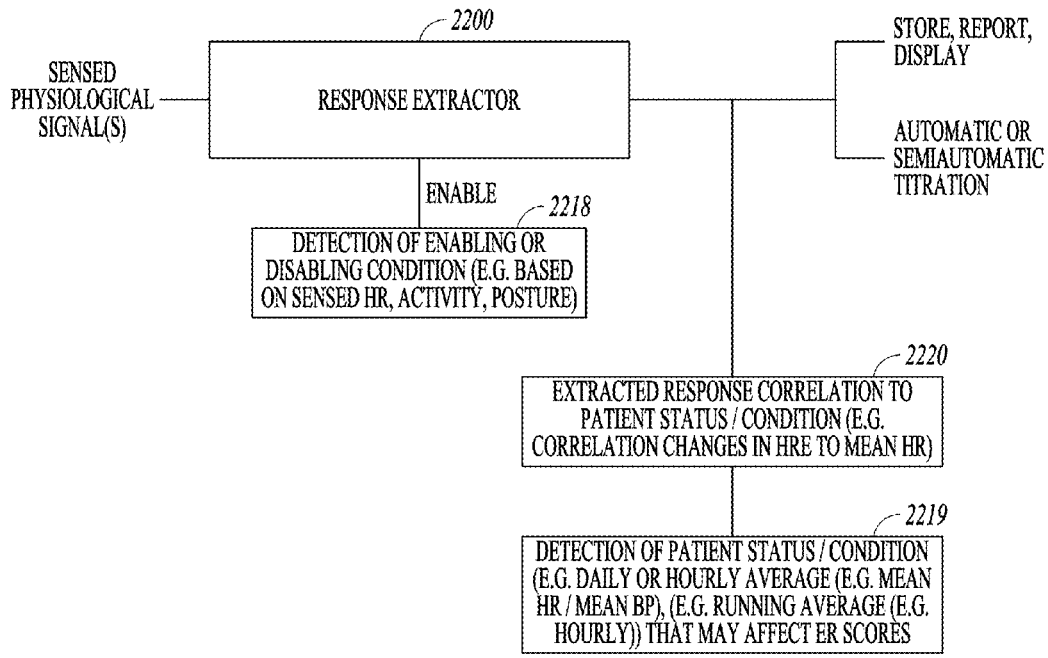
FIG. 22 illustrates, by way of example and not limitation, an embodiment of a response extractor with optional features to enable or disable the response extractions and optional features to correlate an extracted response to a patient status or condition.

FIG. 22 illustrates, by way of example and not limitation, an embodiment of a response extractor with optional features to enable or disable the response extractions and optional features to correlate an extracted response to a patient status or condition. The illustrated response extractor 2200 may function to provide an ANS therapy response extraction process that samples parameter values, analyzes parameter values to score ER value to reference values, and analyzes a group of ER scores to detect subtle and/or inconsistent physiologic response(s). By way of example, the response extractor 2200 of FIG. 22 may be configured to enable and/or disable at least part of the response process based on detected condition 2218. Thus, for example, a system that includes the response extractor 2200 may be configured to use sensed heart rate, sensed activity and/or sensed posture to detect a disabling condition that can disable all or any part of the response process. For example, in response to a detected high activity that may cause the sensed physiological signals to be unusually high, the parameter value sampler, or the parameter value analyzer, or the ER score analyzer, or any combination therapy may be disabled to avoid a potential false detection of a subtle and/or inconsistent physiological response. By way of example, the response extractor may be configured to enable the response process in response to a detected condition that is desirable to provide good, relatively stable, underlying signals to detect the subtle and/or inconsistent physiological response.

Furthermore, by way of example, a system that includes the response extractor may detect a patient status or detect a patient condition 2219. Examples of a status or condition may include a daily or hourly average, such as a mean heart rate or mean blood pressure, that may affect the ER scores. Examples of a status or condition may include a running average (e.g. an average of the period of time such as the last hour). The extracted response from the response extractor 2200 may be correlated 2220 to the detected patient status or patient condition 2219. Thus, for example, changes in a subtle and/or inconsistent heart rate effect (HRE) may be correlated to changes in the mean heart rate. This correlation may be stored, reported or displayed for use by a clinician or other user to monitor autonomic health, and in some embodiments titrate a therapy. The correlations may also be used to provide automatic or semiautomatic titration.

Figure 23:
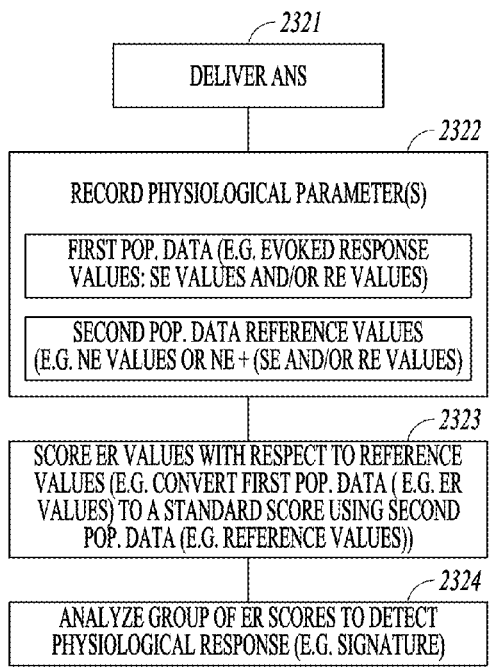
FIG. 23 illustrates, by way of example, a method for titrating VST using a subtle physiologic response.

FIG. 23 illustrates, by way of example, a method for titrating VST using a subtle physiologic response. An autonomic neural stimulation (ANS) therapy may be delivered at 2321. For example, the ANS therapy may be delivered using a nerve cuff or an intravascularly-fed electrode(s) or electrode(s) placed adjacent the target nerve. The ANS therapy may include VST. The VST may target the cervical vagus nerve. The VST may target the vagus nerve in other locations, such as but not limited to, cardiac nerves near the heart or vagal nerves passing by the pulmonary artery(ies). The ANS may target cardiac fat pads. The ANS may target neural targets in and around the carotid sinus such as baroreceptor regions, chemoreceptor regions, the carotid sinus nerve and the glossopharyngeal nerve. The ANS may target neural targets in or near the spinal cord, including the spinal cord, nerve roots, and peripheral nerves extending from the nerve roots. At 2322, physiological parameter(s) that may be affected by the ANS therapy are recorded. The parameter(s) may include first population data and second population data as described previously. The population data may be separated into the first and second population data and stored separately, or may be grouped together, and then processed later to separate the stored data into first and second population data. At 2323, the data may be processed to score ER values (e.g. first population data) with respect to reference values (e.g. second population data). The scoring may be used to quantify a relationship between the ER values and the reference values or an estimate of the relationship. At 2324, a group of ER scores may be analyzed to detect the subtle physiological response. For example, the analysis of the group of ER scores may reflect a desired signature that is associated with an effective therapy.) The group of ER scores may be plotted or trended for use in detecting the subtle physiological response. The group of ER scores may be combined to quantify the subtle physiological response.

Figure 24:
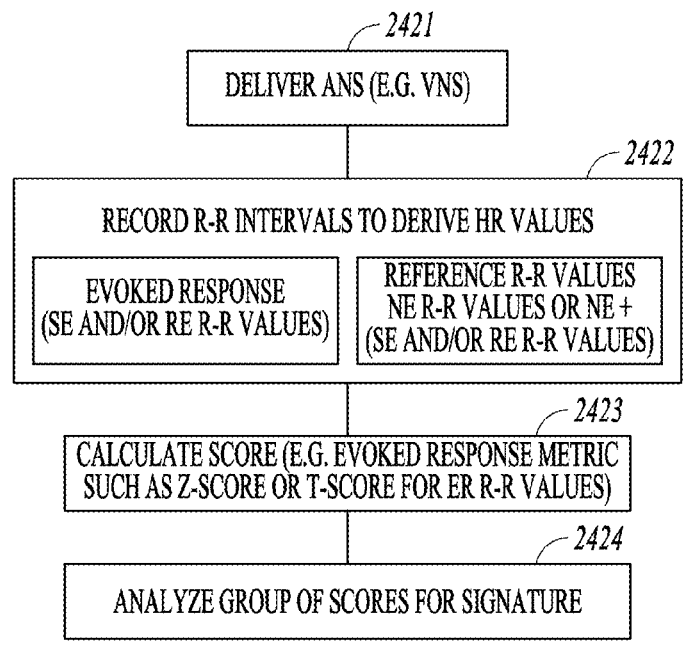
FIG. 24 illustrates, by way of example, a method for monitoring autonomic health using a subtle physiological response to an ANS dose detected using a calculated score.

FIG. 24 illustrates, by way of example, a method for monitoring autonomic health using a subtle physiological response to an ANS dose detected using a calculated score. The ANS (e.g. VNS) may be delivered at 2421. R-R intervals maybe recorded at 2422, allowing the heart rate to be derived therefrom. Evoked response (ER) R-R intervals and reference R-R values may be recorded. At 2423, a score may be calculated for the ER R-R values to quantify a comparison of the ER values to the reference values, and a group of scores may be analyzed for a signature 2424. For example, statistical techniques may be used to quantify this comparison to provide a score. The population data points (e.g. R-R values) may be processed to remove spurious data or other data that is considered to be noise. For example, it may be possible to further refine the quantification of ER values to reference values by being more selective in the data that is used to quantify ER values to reference values. The data may be collected only during a window of time after therapy begins (e.g. after 10 days or other beginning time period and before 50 days or other ending time period). Additionally or alternatively, the data may be collected only during certain windows of time within the burst periods. Additionally or alternatively, the data may be collected only when certain conditions are met (e.g. one or more of mean heart rate, activity, posture, time of day, or other condition is/are within an acceptable range).

The process for detecting R-R intervals may include detecting R peaks and band pass filtering with a cut-off frequency (e.g. 30 Hz, 200 Hz) to remove any DC component, low frequency oscillations and high frequency noise. This filtered signal may then be scored (e.g. Z-score). A Z-score can be found by subtracting the mean of the entire period and normalizing by the standard deviation of the entire period. The Z-scored ECG signal may be rectified to convert negative R peaks into positive peaks. Local maxima may be found using a threshold, and spurious maxima may be removed to allow only one maxima within a window of time for which it is unlikely that two R peaks would be present. The resulting signal may be normalized, and converted into a heart rate signal (r(t)).

$$r(t) = \frac{1}{(t_i - t_{i+1})}$$

The heart rate signal may segmented into segments or groups (e.g. less than 2 interpulse periods or one burst period). For example, the heart rate signal may be segmented into 60 second groups corresponding to one burst period for intermittent ANS delivered using 10 second ON and 50 second OFF stimulation protocol.

$$r(t) = \frac{1}{t_i - t_{i+1}} \forall\ t_i \leq t \leq t_{i+1}$$
$$r_j(t) = r(t + 60j) \forall\ 0 \leq t \leq 60\ \text{seconds}$$

where j represents a trial corresponding to the segment1. The z-score can be calculated for data points at time t within the segment (trial).

$$z(t, j) = \frac{r_j(t) - \overline{r_j}(t)}{std(r_j(t))}$$

Examples of a signature may be seen below.

Figure 25:
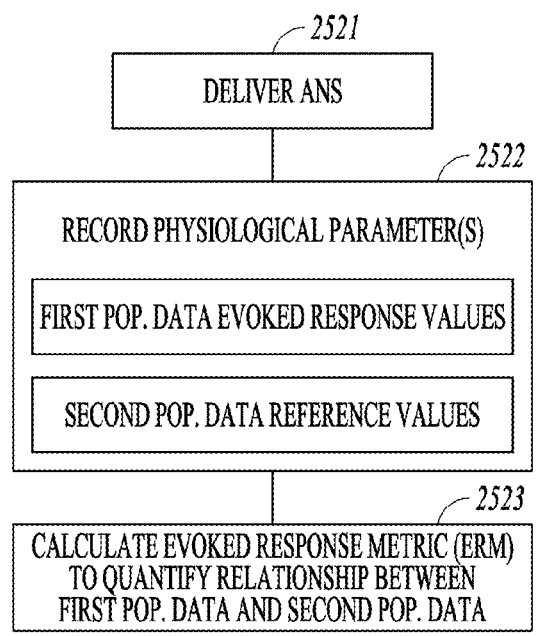
FIG. 25 illustrates, by way of example, a method for monitoring autonomic health using a subtle physiological response to an ANS dose detected using an evoked response metric.

FIG. 25 illustrates, by way of example, a method for monitoring autonomic health using a subtle physiological response to an ANS dose detected using an evoked response metric. The ANS (e.g. VNS) may be delivered at 2521. Physiological parameter(s), such as heart rate, blood pressure, respiration or variability parameters based on heart rate, blood pressure and respiration rate may be recorded at 2522. Evoked response values (part of a first population data) and reference values (part of second population data) may be recorded. At 2523, an evoked response metric (ERM) may be calculated to quantify a comparison of the ER values to the reference values. Various embodiments may use statistical techniques to calculate the ERM to quantify the difference in a first population (with evoked response values) and a second population (with NE values).

Some embodiments may record an electrocardiogram (ECG) (e.g. a P wave, a Q wave, an R wave and an S wave within the cardiac cycle). The QRS waves may be referred to together as a QRS complex. The ECG may be recorded using external electrodes or internal electrodes. Some embodiments sense ECG using electrodes on a can of an implantable device. The PQRS morphology can be analyzed and a change in the PQRS morphology can be calculated to reflect the change from a time before the VNS therapy and during the VNS therapy. An effective therapy can be associated with a desired PQRS morphology change that can serve as a template. The illustrated method checks determine if a current change in PQRS morphology corresponds to the template for the desired PQRS morphology change associated with the effective therapy, and titrates the VNS (or ANS) in an effort to cause the PQRSA morphology change to be closer to the template. The process can be repeated until the PQRS change matches or nearly matches the template for a desired PQRS change that is associated with an effective therapy. Fiducial marks on the PQRS waveforms may be used to detect the change in the PQRS waveform. For example, a difference between a P fiducial for a pre therapy waveform and a waveform during therapy delivery may provide a change in P for comparison to the template. Similarly the differences for a Q fiducial, an R fiducial and an S fiducial can be determined for the pre therapy waveform and the waveform during therapy delivery. A match may be determined if change in the fiducial is sufficiently close (within a threshold) of the corresponding fiducial in the template. More marks for comparison may correspond to a better resolution determining a match.

When VNS is delivered for 10 sec every 60 sec, acute effects on HR may be seen, including a stimulation effect (SE) where HR is acutely lowered for about 10 sec during the stimulation burst, and a rebound effect (RE) where HR is increased for approximately 10 sec following SE.

Figure 26A:
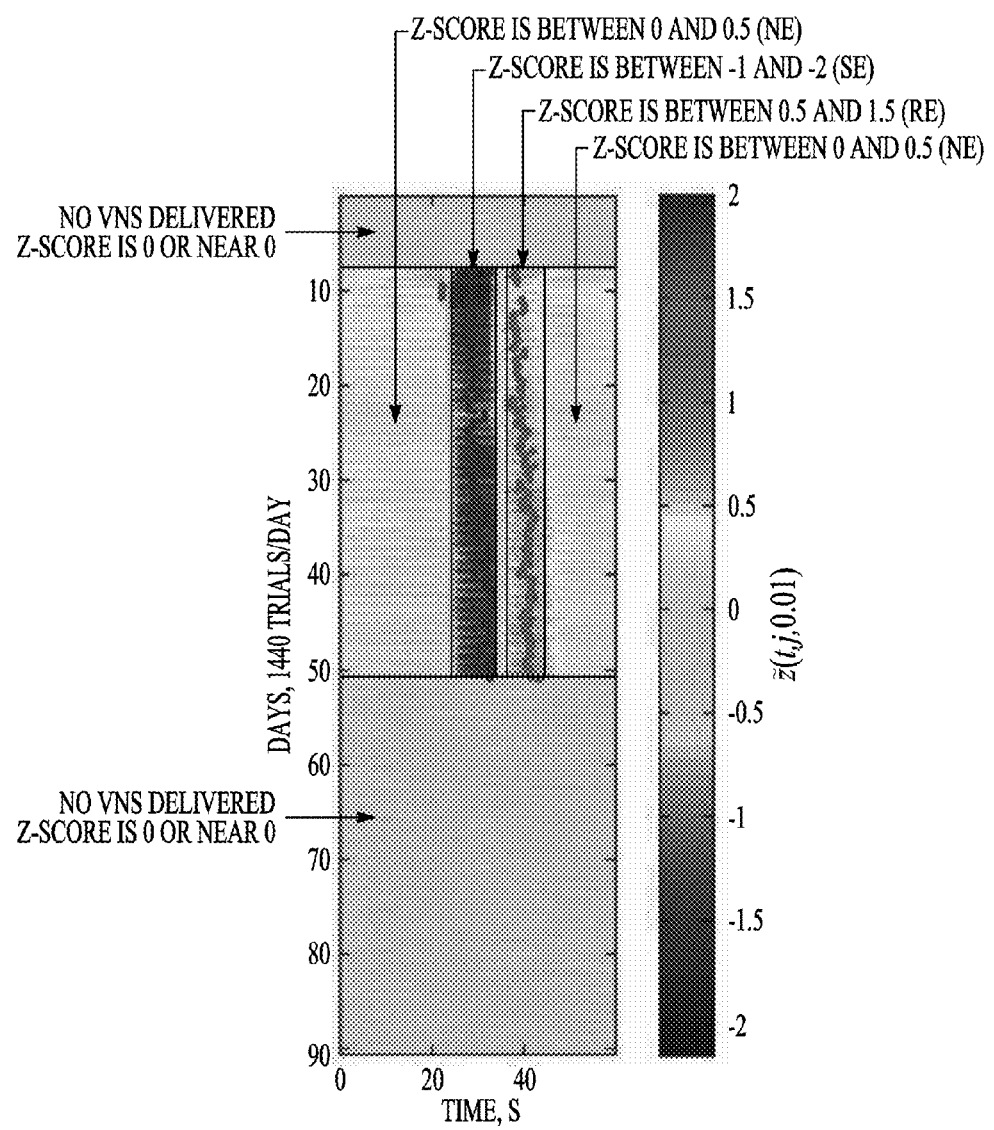
FIGS. 26A and 26B illustrate, by way of example, a heat map ($\bar{z}(t,j, 0.01)$) of Z-scores for a plurality of trials over a number days that provides a visual illustration of a signature for a stimulation effect (SE) and rebound effect (RE), and further illustrates Z-scores at different points along the physiological waveform during the trial.
Figure 26B:
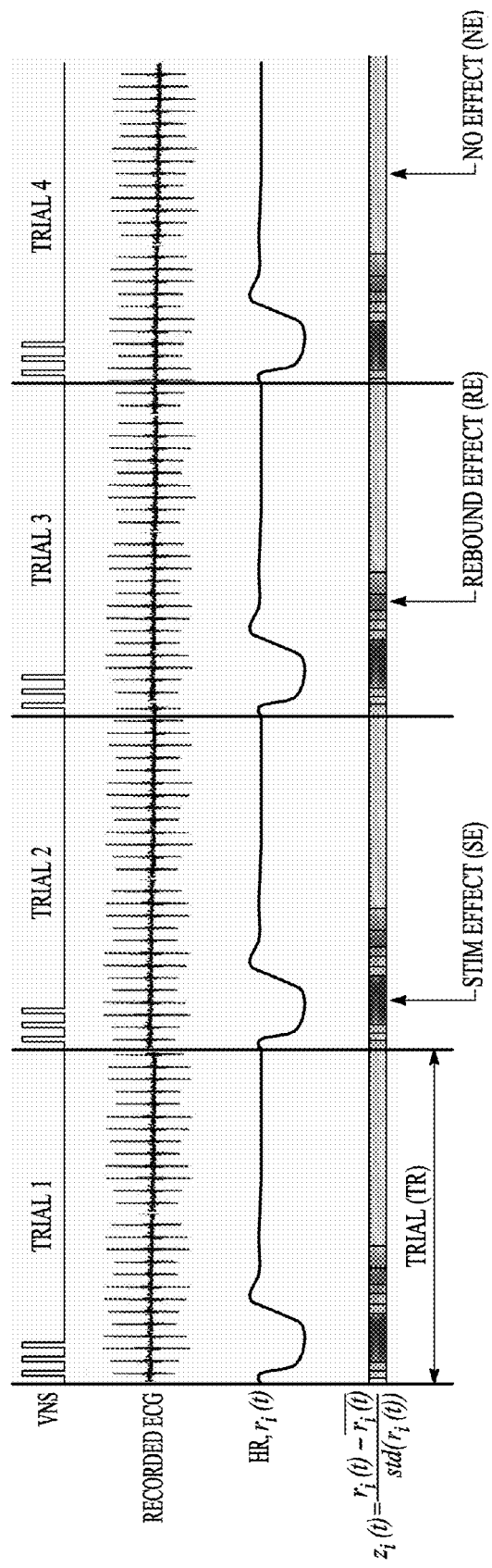

FIGS. 26A and 26B illustrate, by way of example, a heat map ($\overline{z}(t,j), 0.01$)) of Z-scores for a plurality of trials over a number days that provides a visual illustration of a signature for a stimulation effect (SE) and rebound effect (RE), and further illustrates Z-scores at different points along the physiological waveform during the trial. The function ($\overline{z}(t,j), 0.01$)) refers to a filtered version of z(t,j). By way of example, the filtered version may have a cut-off frequency such as a cut-off frequency of 0.01 (or an average over 100 trials). The heat map may be displayed using multiple colors to show the gradation of Z-scores. A Z-score identifies the difference between a current data point and the mean using standard deviation. Thus, a Z score of "1" indicates the score has a value that is one standard deviation higher than the mean, and a Z score of "−1" indicates the score has a value that is one standard deviation less than the mean. In the illustrated example, VNS was not delivered during the first several days (e.g. 7 days) and was stopped after about 50 days. The trial period corresponds to the 60 second burst period for the intermittent stimulation, such that each day has 24 hr×60 min/hr=1440 trials per day. The SE time, illustrated within Trial 2 for FIG. 26B, indicates that the Z-score within this time frame is between −1 and −2. The RE time, illustrated within Trial 3 for FIG. 26B, indicates that the Z-score within this time frame is between 0.5 and 1.5 The NE time, illustrated in Trial 4 for FIG. 26B, illustrates that the Z-score within this time frame has a small magnitude (e.g. 0-0.5). The heat map illustrated in FIG. 16A illustrate a signature for the SE and a signature for the RE within a burst period. Various embodiments adjust the ANS to cause the signature to match a desired signature that is effective for a given therapy (e.g. heart failure or hypertension). By way of example and not limitation, a desired subtle response may be identified using a magnitude of the change, or a direction of the change, or a percent time that the changes are detectable, or the presence of absence of a reflex effect (RE), or a combination of these factors (e.g. significant Z-score but with a minimal magnitude of change).

Figure 27A:
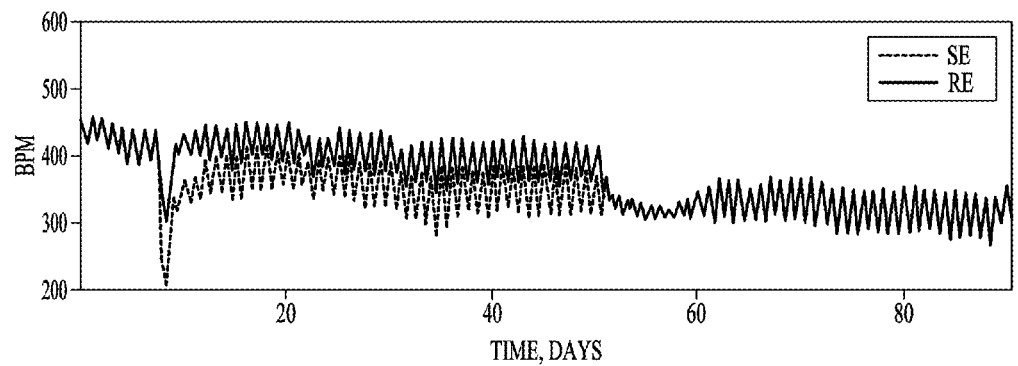
FIGS. 27A-27C illustrate additional examples for quantifying a comparison between the SE and the reference values.
Figure 27B:
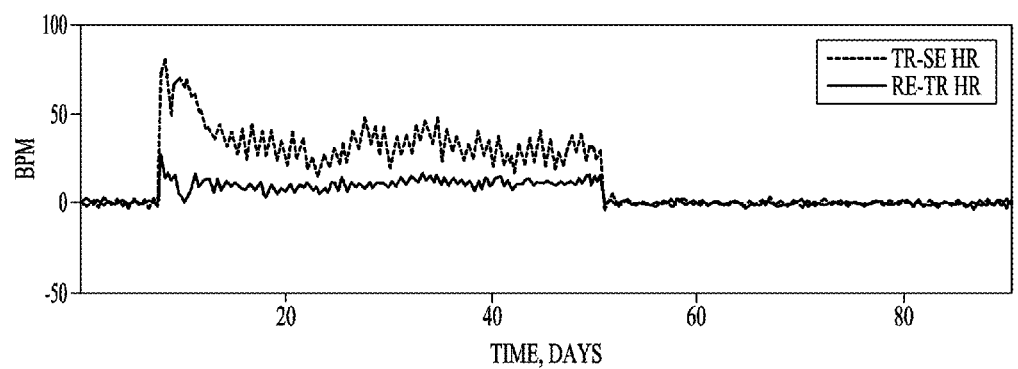
Figure 27C:
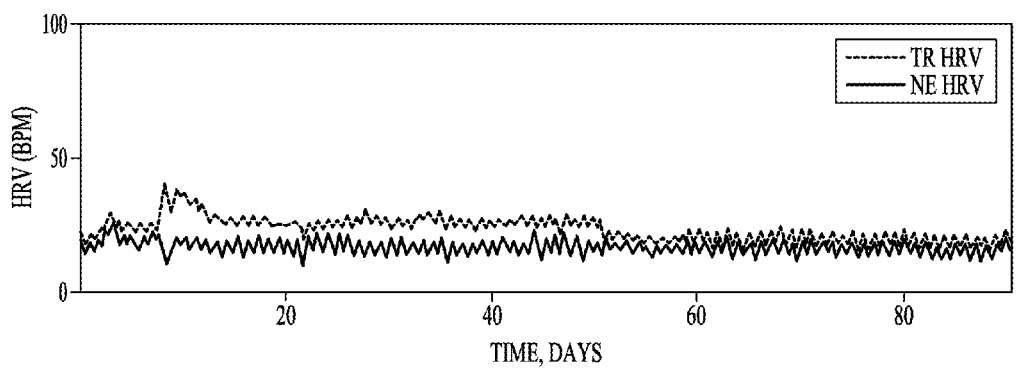

FIGS. 27A-27C illustrate additional examples for quantifying a comparison between the SE and the reference values. In the illustrations, the SE values are lower than the RE values (FIG. 27A), the magnitude of the difference for the SE is larger than the RE values, and the variability increases during the times of the evoked response, which includes both the SE and RE values. FIG. 27A illustrates heart rate (HR) as a function of time calculated by averaging over trial (TR), SE and RE zones. FIG. 27B illustrates a heart rate (HR) difference between a trial (TR) and stimulation effect (SE), and a HR difference between a reflex effect (RE) and trial (TR). FIG. 27C illustrates HRV, in beats per minute, for a trial and HRV for no effect (NE).

Template profiles may be used to create several biomarkers. Biomarkers may be used to provide a reference for monitoring autonomic health. Biomarkers may be used to identify an effective ANS therapy such as but not limited to average, acute, chronic magnitude of TR, SE, RE, TR-SE RE-TR HR and NE, TR HRV, magnitude of high, low, very low, very very low, very very very low frequencies HRV.

Figure 28:
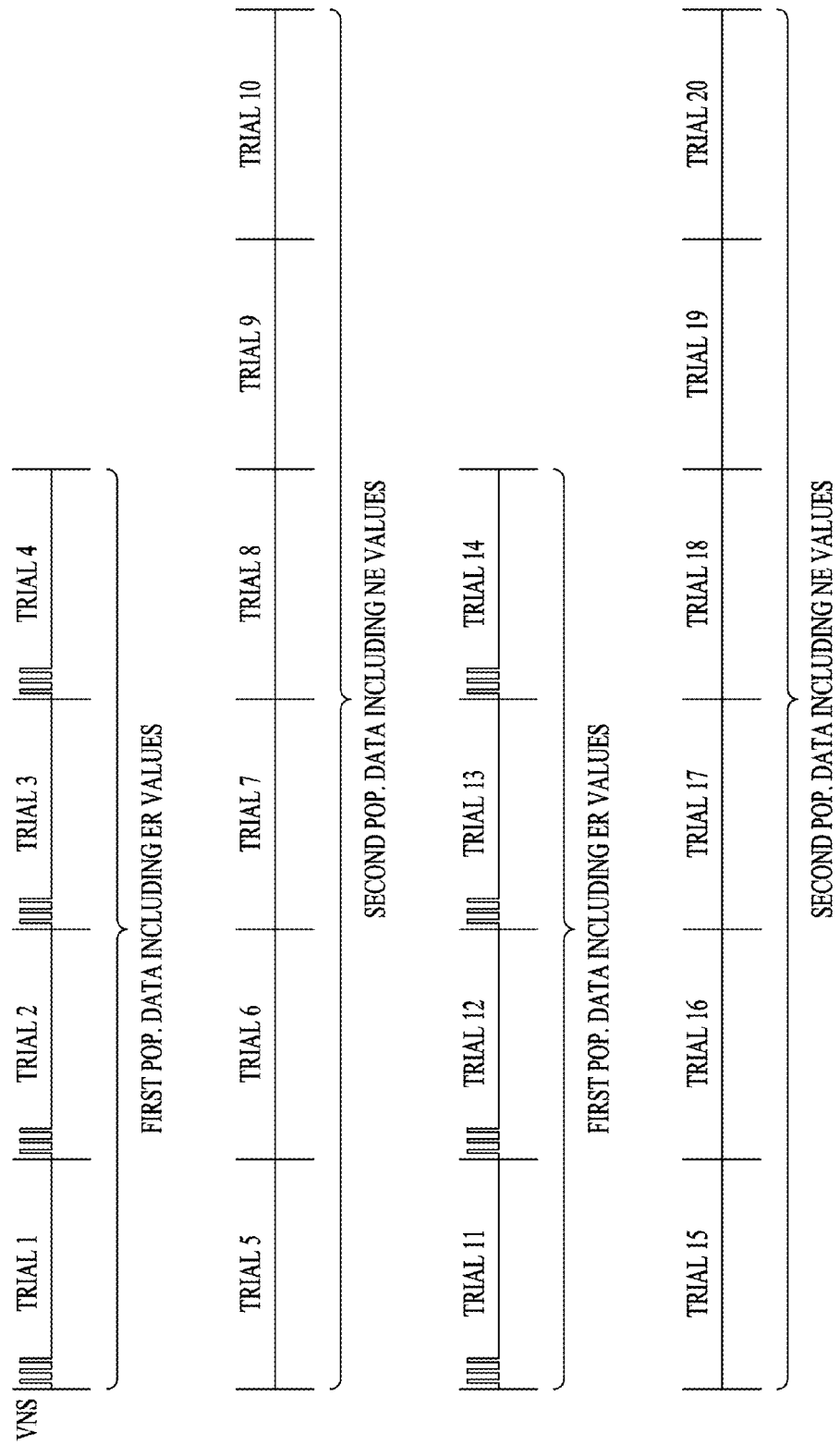
FIG. 28 illustrates, by way of example, ANS dose timing to provide another way in which the first and second population data may be captured.

FIG. 28 illustrates, by way of example, ANS dose timing to provide another way in which the first and second population data may be captured. The illustrated ANS dose includes intermittent stimulation during 4 trials (burst periods), followed by 6 trials (burst periods) without neural stimulation. The first population data may be taken during one or more of the first 4 trials which include neural stimulation bursts, and the second population data may be taken during one or more of the subsequent 6 trials which do not include neural simulation bursts.

Some embodiments may titrate the ANS dose to determine a smallest dose magnitude that can still provide a detectable physiological effect. Some embodiments may adjust the timing in which the first and second population data is collected. For example, the first population data may change from data during the stimulation burst to during the stimulation burst and some time after the stimulation burst. Some embodiments may adjust the trial length from being the same as the burst period (e.g. 60 seconds) to a length greater the burst period, but may still be less than two burst periods. Thus, for example, NE values may be detected for some time before and after ER values. Some embodiments may score the ER values to look for acute effects (e.g. burst to burst effects). Some embodiments may look for chronic changes by turning on ANS for a longer period of time (e.g. 5 to 20 minutes) in which first population data may be recorded and off for a longer period of time (e.g. 5 to 60 minutes) in which second population data may be recorded to look for a signature in the relationship between the first and second population data.

A device may capture data using various techniques. For example, sensed physiological data may be stored, and data marks or time marks may be added for use to identify when simulation is applied. Some embodiments may store the raw data (e.g. R-R intervals). Some embodiments only record a sample size needed to detect the signature. Thus, for example, if the signature is present for a given percentage of time, then one can expect to detect that signature after so many trials.

Some embodiments may monitor a percentage of time that a detectable signature is present. For example, when the signal is detected a greater percentage of time, then one may conclude that the underlying background of autonomic activity is changing. For example, when the stimulation is a vagal stimulation and the signal is detected a greater percentage of time, one may conclude that the underlying background is becoming more sympathetic. When the stimulation is a vagal stimulation and the signal is detected a smaller percentage of time, one may conclude that the underlying background is becoming less sympathetic.

The response monitor may be remotely managed and programmed. Thus, for example, a patient may wear external ECG electrodes to collect data while they are away from a clinical setting. Patient conditions or activities or time may also be monitored. The ECG data may be tagged with the patient conditions or activity or time. For example, the ECG data may be stored with data indicating if the ECG data was collected for a particular patient posture or a particular patient activity or a particular time of day.

Figure 29:
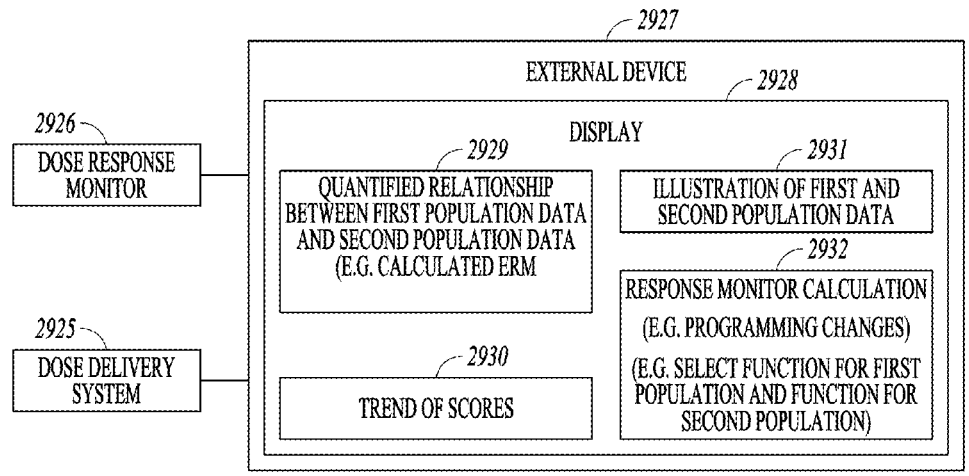
FIG. 29 illustrates, by way of example, an embodiment of a system that includes an ANS dose delivery system, a dose response monitor, and an external device.

FIG. 29 illustrates, by way of example, an embodiment of a system that includes an ANS dose delivery system 2925, a dose response monitor 2926, and an external device 2927.

The external device 2927 may have a user interface, of which a component may be a display 2928. The display may be a touch screen display. The display may output information to the user (patient, or clinician or other caregiver), for use in monitoring autonomic health. For example, as illustrated at 2929, the display may output the quantified relationship (e.g. calculated ERM) between the first and second population data. The display may output a trend of scores (e.g. ERM scores) 2930. The display may illustrate or otherwise identify the make-up of the first and second population data 2931. For example, the display may identify whether the first and second population data are exclusive sets of data, if they have a union of data points, or if one set encompasses all of the other set. The display may identify the relative position of the first and/or second population data with respect to the neural stimulation bursts (e.g. coextensive with the bursts, during a portion of the burst, over the course of 4 burst periods, etc.). The display may also provide an indication of the response monitor calculation 2932. For example, recommended programming changes and/or potential programming changes may be made based on the reported scores. The display may also identify the function applied to the population to determine the ERM scores, and/or identify potential functions that may be applied to the population.

Figure 30:
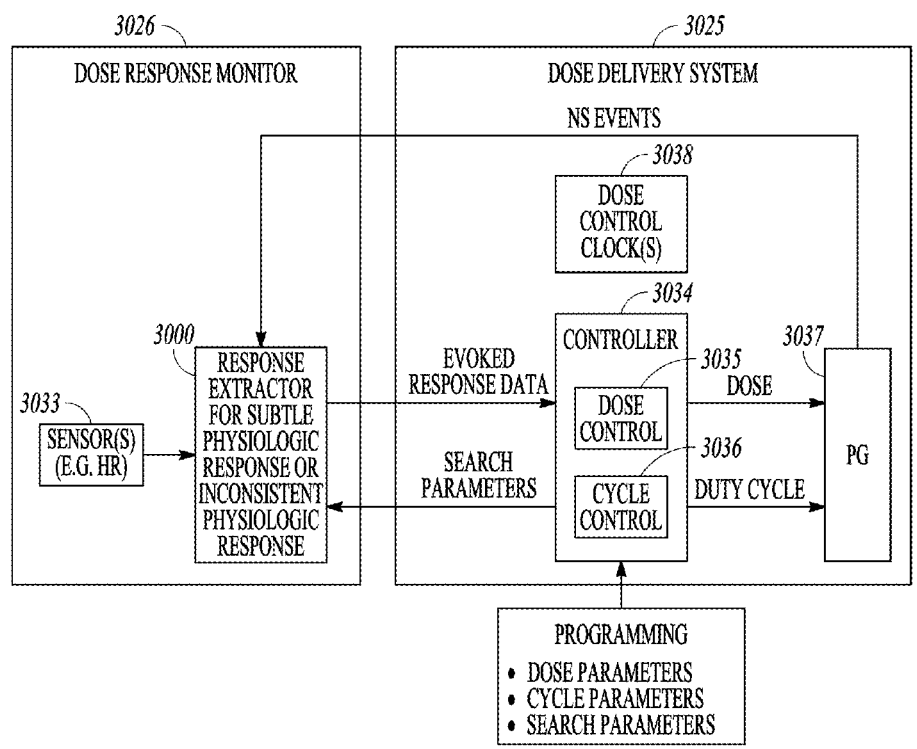
FIG. 30 illustrates a system embodiment configured to extract an evoked response and control stimulation using the extracted response.

FIG. 30 illustrates a system embodiment configured to extract an evoked response and control stimulation using the extracted response. Various device embodiments include an ANS dose delivery system 3025, a dose response monitor 3026 (which may be similar to the response monitor 2926 in FIG. 29) with a response extractor 3000 (which may be similar to the response extractors in previous figures) that is capable of providing feedback from sensors 3033 (e.g. HR sensor). The ANS dose delivery system 3025 may also be configured to delivery an ANS therapy in addition to delivering an ANS dose for use in monitoring autonomic health. Examples of ANS therapy include neural stimulation to the vagus nerve (VNS), carotid sinus nerve, glossopharyngeal nerve, baroreceptor regions, chemoreceptor regions, spinal cord, and nerve roots. The ANS therapy can directly or reflexively modulate heart rate, for example. The response extractor 3000 can extract a representation of the evoked response by determining how the heart rate and/or blood pressure response during times of stimulation (e.g. a burst of neural stimulation pulses) compares to the responses during times without stimulation. The controller 3034 may be configured to modulate the neurostimulation dose 3035 (e.g. charge delivered over a period of time) and/or duty cycle 3036. The controller 3034 may control the pulse generator 3037 to control the pattern of pulses delivered to the patient. In some embodiments, the pulse generator 3037 or controller 3034 may provide a marker ("NS Event" marker) to the response extractor for use to time the start and stop times for recording physiological data.

The effect of the neural stimulation on HR or BP may controlled by the NS dose, which consists of a complex set of variables, including electrode design, stimulation site, pulse amplitude, width and phase, pulse burst duration and pattern, stimulation timing, and the like. The selection of NS dose may depend on the therapeutic application of the device. In some applications, the NS dose may be selected to decrease or increase HR or BP by directly stimulating neural pathways that control HR or BP. This in turn may result in compensatory reflex changes in HR or BP after the NS event ends. In such cases, the NS event may cause an oscillation of HR or BP that lasts for several seconds or minutes. These are oscillatory evoked responses. They may be preferred in some applications of the device to deliver a combination of directly stimulated and reflex changes in ANS activity. By altering the NS dose, the device can control the magnitude, pattern, and duration of the evoked responses. A device response extractor can measure these evoked response parameters to be used by a controller to adapt the NS dose to achieve a desired evoked response that is subtle and/or inconstant, detectable using statistical techniques to determine an ERM score.

Sensors 3033 may provide a continuous stream of signal data to the response extractor 300. This data stream can be digitized into a discrete time series for analysis. The response extractor 3000 may be notified of each intermittent NS event, and use these events to record or process the signal time series to provide the first and second population data. Multiple NS events may be analyzed to provide evoked response data to the controller 3034. The controller 3034 may use this data according to programmed parameters to control the duty cycle and/or the dose of the neurostimulation. The controller may be programmed to adjust the NS dose until the evoked response data match programmed criteria (signature or ERM score). The controller 3034 may provide search parameters to the response extractor 3000 to control its functions, such as to set search criteria or search windows for the extraction algorithms, or request which evoked response data are to be extracted, among other possibilities.

The illustrated system may also include dose control clock(s) 3038 to control the processes performed by the system. For example, the clock(s) 3038 may include dose control clock(s) for use to control the timing of the neural stimulation pulses delivered in the bursts of pulses, and to also control the timing of the neural stimulation burst of pulses such as burst start, burst stop, burst duration, or various combinations thereof. The therapy protocol clock(s) may also control a schedule of neural stimulation dose. Some embodiments use a timer and a programmed schedule to adjust VNS dose. The clock(s) 3038 may include a VNS suspension clock or clocks for use to control timing of stimulation suspensions. The stimulation suspensions may override scheduled VNS times. For example, a patient may indicate, via remote control or other external device, by "tapping" over the implantable device, by a magnet, or otherwise, a desire to suspend VNS because the VNS is not being tolerated or because the VNS may interfere with an activity (e.g. speaking, eating, etc.). Some embodiments may, additionally or alternatively, suspend therapy for specific patient conditions. By way of example and not limitation, the patient condition may be a respiration infection or sore throat caused by a virus or another condition for which a VNS may be more aggravating. The therapy suspension clock can time the temporary suspension and reengage the scheduled therapy after the suspension. The therapy suspension may be triggered by a dose monitor. For example, once the desired level of stimulation has been delivered for a given period of time (e.g. daily dose of stimulation), then the dose monitor may suspend the therapy for the remainder of that time (e.g. remainder of the day).

Figure 31:
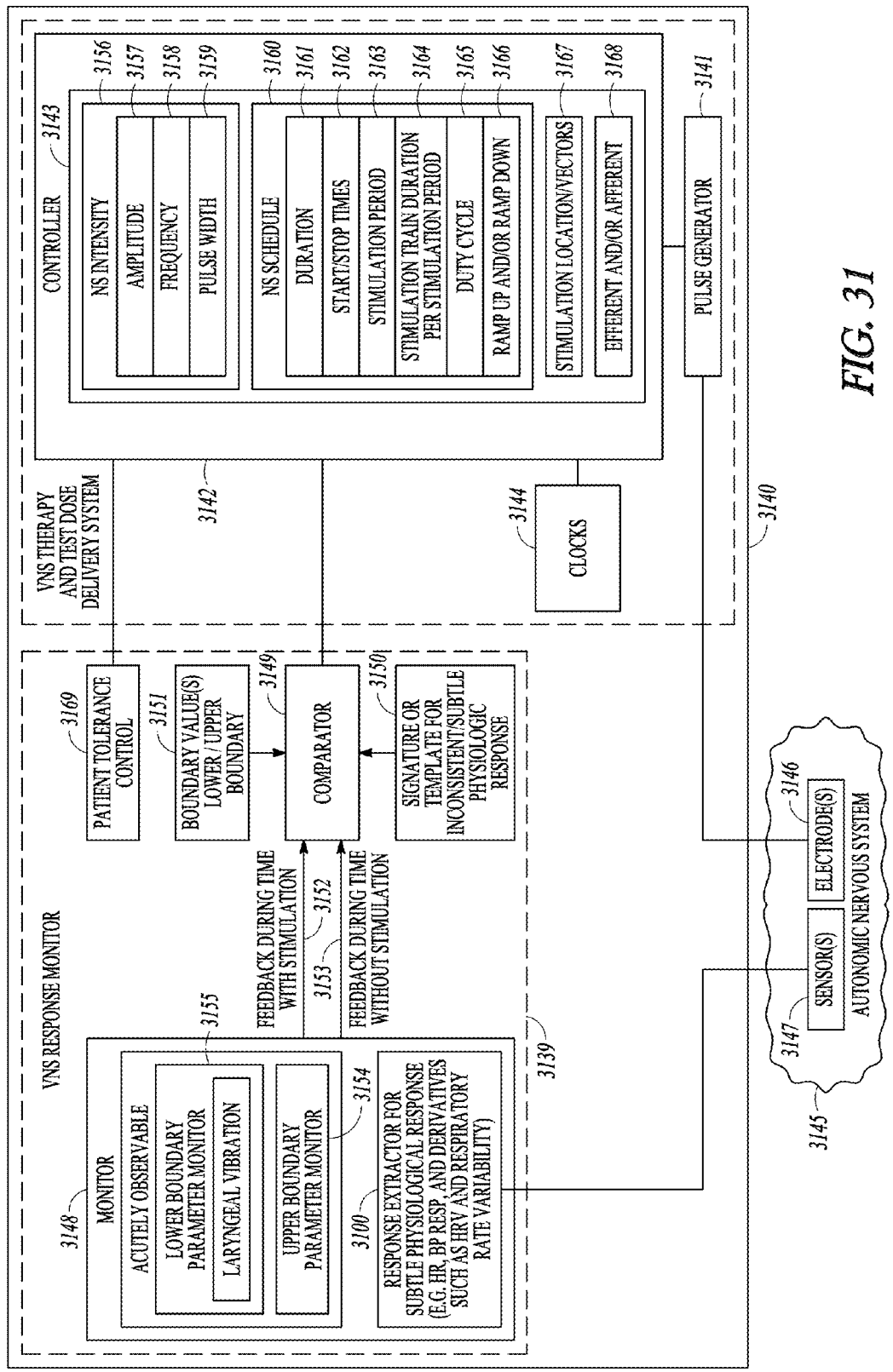
FIG. 31 illustrates a VNS system, according to various embodiments.

FIG. 31 illustrates a VNS system, according to various embodiments. The VNS system is an example of an ANS system. An implantable device may provide the entire VNS system. Some embodiments use external devices to provide the monitoring functions or some of the monitoring functions, such as during implantation of an implantable vagus nerve stimulator. The illustrated VNS system includes VNS response monitor 3139 and a VNS therapy and test dose delivery system 3140. It is noted that the VNS intensity for the test dose to monitor autonomic health may be independent of the VNS intensity delivered as part of the VST.

The VNS therapy and test dose delivery system may include a pulse generator 3141 to provide VNS therapy, a controller 3142 configured with a modulator 3143 to change or modulate intensity of the VST and clocks 3144. The system may further include a VNS response monitor 3139 to provide feedback which may be used to allow the patient, clinician or other caregiver to program adjustments or which may be used to provide automatic or semiautomatic programming adjustments. The autonomic nervous system is generally illustrated at 3145. Appropriate electrode(s) 3146 are used to provide desired neural stimulation and sensor(s) 3147 to sense a parameter that is affected by the neural stimulation. Physiological parameter(s) that quickly respond to VST can be used in closed loop systems or during the implantation process. Examples of such parameters include heart rate, laryngeal vibration, blood pressure, respiration, electrogram parameters. Other cardiovascular parameter(s) and other surrogate parameters that have a quick and predictable response indicative of the overall response of the parasympathetic nervous system to the neural stimulation. Other parameter(s) that have a slower response may be used to confirm that a therapeutically-effective dose is being delivered. The sensor(s) and electrode(s) can be integrated on a single lead or can use multiple leads. Additionally, various system embodiments implement the functions using an implantable neural stimulator capable of communicating with a distinct or integrated implantable cardiac rhythm management device.

The VNS response monitor 3139 may include a monitor 3148, a comparator 3149, and may further included a programmable targeted signature or template of a subtle and/or inconsistent response 3150, and may include programmable boundary value(s) 3151 that may limit the adjustments during a titration routine. The illustrated monitor 3148 monitors the parameter during a time with stimulation to provide a first feedback signal 3152 indicative of a parameter value corresponding to a time with stimulation and during a time without stimulation to provide a second feedback signal 3153 indicative of a parameter value corresponding to a time without stimulation. The signals 3152 and 3153 are illustrated as separate lines. These signals can be sent over different signal paths or over the same signal path. A comparator 3149 receives the first and second feedback signals 3152 and 3153 and determines a detected change in the parameter value based on these signals. Additionally, the comparator compares the detected change with an allowed change, which can be programmed into the device. For example, the device can be programmed to allow a heart rate reduction during VST to be no less than a percentage (e.g. on the order of 95%) of heart rate without stimulation. The device may be programmed with a quantitative value to allow a heart rate reduction during VST to be no less than that quantitative value (e.g. 5 beats per minute) than heart rate without stimulation. The monitor 3148 may include a response extractor 3100, similar to previously-described response extractors that analyzes a first population of data that includes data during the time with stimulation and a second population of data that includes data during the time without stimulation. The response extractor may calculate an ERM score or otherwise quantify a relation between the first and second populations. The comparator 3149 may compare the ERM score from the response extractor (or other quantified score) to the targeted signature 3150 for the subtle response and provide a comparison result to the controller 3142.

As illustrated, the system may be programmed with an upper boundary value 3151 corresponding to a monitored parameter value used to provide an upper boundary on VST intensity, and the VST response monitor 3139 may include an upper boundary parameter monitor 3154. The upper boundary parameter monitor provides a signal indicative of a sensed value for the parameter, which is compared to the upper boundary value. The VST intensity is adjusted to be below the upper VST intensity, as detected using the upper boundary value and upper boundary parameter monitor. The upper boundary value may be pre-programmed based on patient-specific responses to VST or based on data for a patient population. The illustrated embodiment monitors heart rate, and compares sensed heart rate to a preprogrammed heart rate corresponding to an upper boundary for VST intensity. The system may also be programmed with a lower boundary value 3151 corresponding to a monitored parameter value used to provide a lower boundary on VST intensity, and the VST response monitor 3148 includes a lower boundary parameter monitor 3155. The lower boundary parameter monitor provides a signal indicative of a sensed value for the parameter, which is compared to the lower boundary value. The VST intensity is adjusted to be above the lower VST intensity, as detected using the lower boundary value and lower boundary parameter monitor. The lower boundary value may be pre-programmed based on patient-specific responses to VST or based on data for a patient population. The illustrated embodiment monitors laryngeal vibration.

Some embodiments use a therapy protocol that adjusts the VST intensity, limited by the upper boundary for the VST intensity and in some embodiments by the lower boundary for the VST intensity, to provide the targeted signature for the subtle response. The VST intensity can be adjusted, within the allowed bounds set by the present subject matter, based on other parameters such as blood pressure, respiration, and electrogram measurement. Some therapy protocols adjust the targeted subtle response, and may also adjust the upper boundary and/or lower boundary for VNS therapy intensity based on a schedule (e.g. time of day) or sensed data (e.g. activity). Some examples of programmable parameters that may be used and modified based on an evoked response can include parameters used to adjust the intensity of the neural stimulation 3156, such as amplitude 3157, frequency 3158, pulse width 3159. Some embodiments adjust the neural stimulation schedule 3160 to adjust the neural stimulation intensity. Examples of schedule parameters 3160 include therapy duration 3161 (e.g. how many minutes the INS therapy protocol is delivered), start/stop times 3162 (e.g. when to start or stop the INS therapy protocol), stimulation period 3163 (e.g. the burst interval of the INS therapy protocol), stimulation train duration per stimulation period 3164 (e.g. the burst duration of the INS therapy protocol), duty cycle 3165 (e.g. the stimulation duration/stimulation period of the INS therapy protocol), and a ramp up and/or ramp down 3166 for the intensity of the stimulation burst. Some embodiments are designed with the ability to operationally position a plurality of electrodes near the neural pathway to stimulate different locations along the neural pathway to initiate an action potential at these different locations along the neural pathway. As generally illustrated at 3167, some embodiments change where the nerve is stimulated and/or the vectors used to change the distance that the action potential has to travel before inducing a response, and thus changes the timing of the response induced by the action potential for a direct response or a reflex response. Some embodiments control whether an efferent or afferent pathway is being stimulated, as illustrated generally at 3168. Some embodiments may change VNS intensity by targeting different nerve fiber populations. By way of example and not limitation, different nerve fibers may be targeted by adjusting the stimulation field by current steering and/or changing electrodes. Adjustment of these parameters may be used to adjust the evoked response (e.g. stimulation effect and reflex).

As illustrated, the system may include a patient tolerance control 3169 which may be an input for responding to a patient signal or an input to receive a signal from the system if the system can detect or derive that the patient is unable to tolerate the therapy. The controller may respond by maintaining the pulse amplitude by but reducing the overall dose by reducing other parameter(s) (e.g. frequency, or pulse width, or various scheduling parameters.) The neural stimulation delivered during the duty cycle can be delivered using a variety of neural stimulation techniques, such as stimulation that uses electrical, ultrasound, thermal, magnetic, light (optigenetics) or mechanical energy (such as acupuncture). Electrical neural stimulation is used in this document as an example of neural stimulation. In electrical stimulation, for example, a train of neural stimulation pulses (current or voltage) can be delivered during a duty cycle of stimulation. Stimulation pulse waveforms can be square pulses or other morphologies. Additionally, the stimulation pulses can be monophasic or biphasic pulses.

The illustrated system for delivering VNS therapy may useful in extended therapy applications. Examples of extended therapy applications involve applying stimulation to prevent remodeling of cardiac tissue and to reverse remodel cardiac tissue in cardiovascular disease. VNS therapy can be applied for a portion (approximately 10 seconds) of each minute, for example. A VNS therapy dose may be adjusted by adjusting the duration or duty cycle of the stimulation (e.g. approximately 5 seconds or 15 seconds each minute or approximately 5 to 15 seconds every 30 seconds or approximately 5 to 30 seconds every 2 minutes, or approximately 5 seconds to 3 minutes every 5 minutes or a continuous stimulation). According to an embodiment, the VNS therapy non-selectively stimulates both efferent and afferent axons. The illustrated values are provided by way of example, and not limitation. Over the course of days, weeks, months and years, the physiological response to VNS therapy can vary for a number of reasons, such as nerve adaptation, tissue encapsulation, fibrosis, impedance changes, and the like. Further, the patient health and disease state may change. Additionally, the activity or other status or condition of the patient may also change. Therefore, it is desirable to be able to quantify the evoked response of the stimulation to make adjustments that accommodate these changes.

Open loop VST systems set the VST intensity during VST testing. This VST testing may be based on a relatively large human population or may be performed during the implantation procedure. By way of example, VST intensity for an open loop system may be titrated as follows. When VST is turned on for the first time, the heart rate is monitored during testing. If there is any significant bradycardia (e.g. more than a 5% drop in heart rate) during the ON time of VST cycle, VST intensity (also referred to as VST dose) will be reduced. The VST dose can be reduced by adjusting one or more VST parameters such as amplitude, frequency, pulse width, etc. During the follow-up office visits for therapy titration, VST parameters may be adjusted to provide a therapeutically-effective dose at a targeted subtle therapeutic response.

Figure 32:
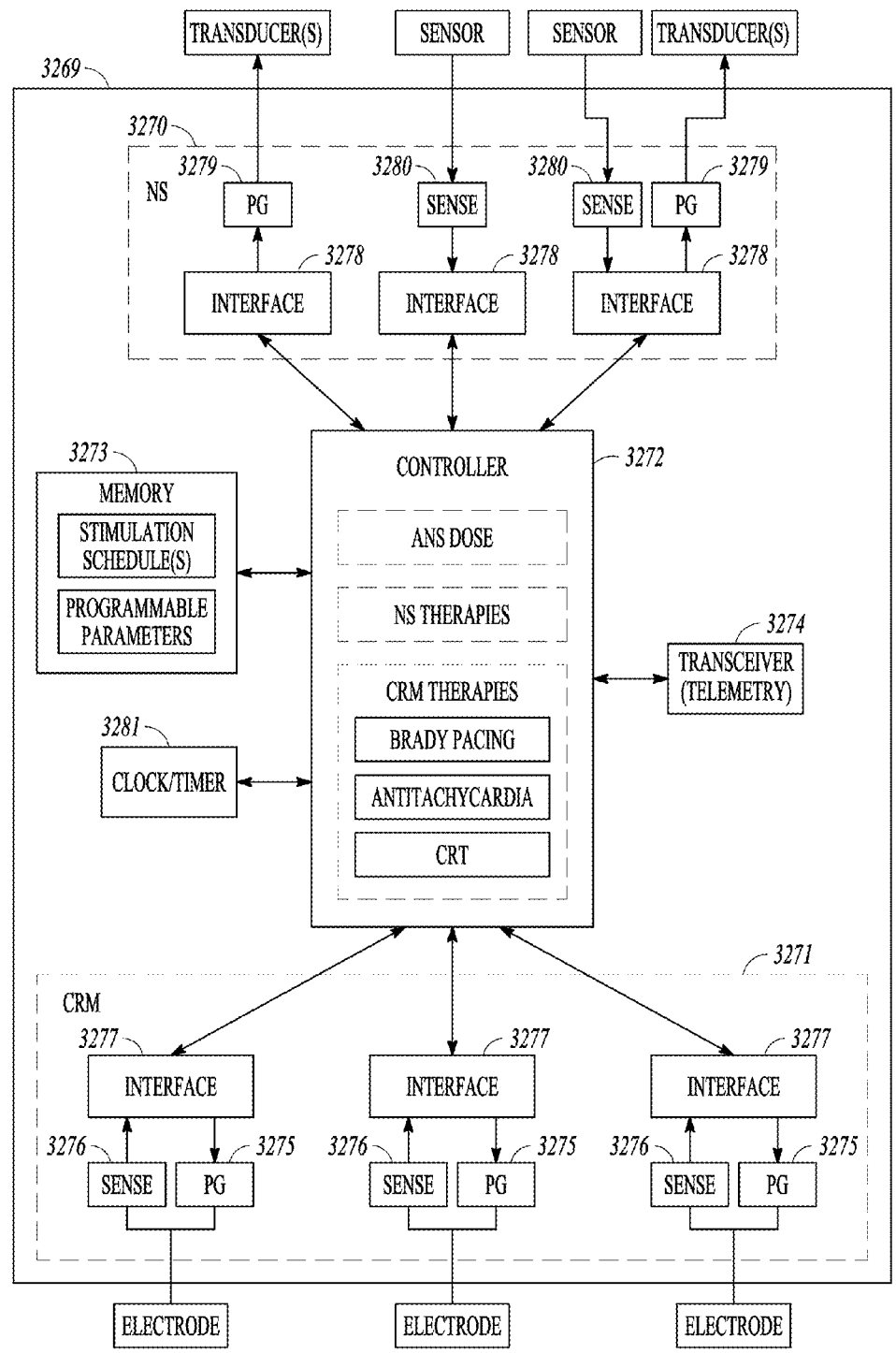
FIG. 32 illustrates an implantable medical device (IMD) having a neural stimulation (NS) component and a cardiac rhythm management (CRM) component according to various embodiments of the present subject matter.

FIG. 32 illustrates an implantable medical device (IMD) 3269 having a neural stimulation (NS) component 3270 and a cardiac rhythm management (CRM) component 3271 according to various embodiments of the present subject matter. The illustrated device includes a controller 3272 and a memory 3273. According to various embodiments, the controller includes hardware, software, firmware or a combination thereof to perform the neural stimulation and CRM functions. For example, the programmed therapy applications discussed in this disclosure are capable of being stored as computer-readable instructions embodied in memory and executed by a processor. For example, stimulation schedule(s) and programmable parameters can be stored in memory. According to various embodiments, the controller includes a processor to execute instructions embedded in memory to perform the neural stimulation and CRM functions, as well as the ANS dose delivered to monitor autonomic health. The illustrated neural stimulation therapy can include various neural stimulation therapies, such as a heart failure therapy or a hypertension therapy. Various embodiments include CRM therapies, such as bradycardia pacing, anti-tachycardia therapies such as ATP, defibrillation and cardioversion, and cardiac resynchronization therapy (CRT). The illustrated device further includes a transceiver 3274 and associated circuitry for use to communicate with a programmer or another external or internal device. Various embodiments include a telemetry coil.

The CRM therapy section 3271 includes components, under the control of the controller, to stimulate a heart and/or sense cardiac signals using one or more electrodes. The illustrated CRM therapy section includes a pulse generator 3275 for use to provide an electrical signal through an electrode to stimulate a heart, and further includes sense circuitry 3276 to detect and process sensed cardiac signals. An interface 3277 is generally illustrated for use to communicate between the controller 3277 and the pulse generator 3275 and sense circuitry 3276. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 3270 includes components, under the control of the controller, to stimulate a neural stimulation target and/or sense parameters associated with nerve activity or surrogates of nerve activity such as blood pressure, heart rate and respiration. Three interfaces 3278 are illustrated for use to provide neural stimulation. However, the present subject matter is not limited to a particular number interfaces, or to any particular stimulating or sensing functions. Pulse generators 3279 are used to provide electrical pulses to transducer or transducers for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, sinusoidal wave, and waves with desired harmonic components. Sense circuits 3280 are used to detect and process signals from a sensor, such as a sensor of nerve activity, blood pressure, respiration, and the like. The interfaces 3278 are generally illustrated for use to communicate between the controller 3272 and the pulse generator 3279 and sense circuitry 3280. Each interface, for example, may be used to control a separate lead. Various embodiments of the NS therapy section only include a pulse generator to stimulate a neural target. The illustrated device further includes a clock/timer 3281 or multiple clocks/timers, which can be used to deliver the programmed therapy according to a programmed stimulation protocol and/or schedule and to suspend therapy. The controller 3272 may include a response extractor, and may also control the therapy according to programmable therapy dose, duty cycle, and search parameters, as discussed previously.

Figure 33:
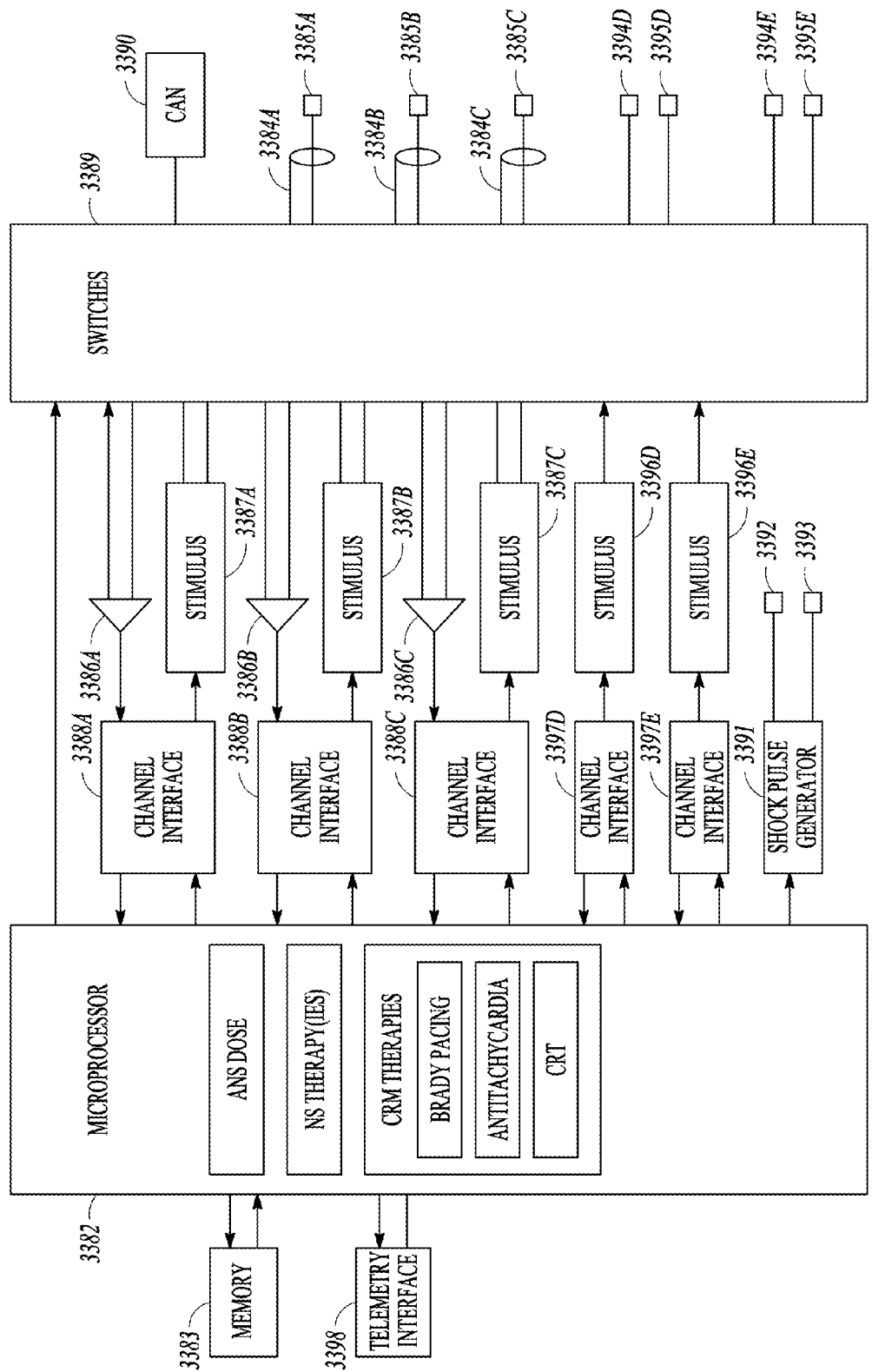
FIG. 33 shows a system diagram of an embodiment of a microprocessor-based implantable device, according to various embodiments.

FIG. 33 shows a system diagram of an embodiment of a microprocessor-based implantable device, according to various embodiments. The controller of the device is a microprocessor 3382 which communicates with a memory 3383 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 3384A-C and tip electrodes 3385A-C, sensing amplifiers 3386A-C, pulse generators ("stimulus") 3387A-C, and channel interfaces 3388A-C. Each channel thus includes a pacing channel made up of the pulse generator connected to the electrode and a sensing channel made up of the sense amplifier connected to the electrode. The channel interfaces 3388A-C communicate bidirectionally with the microprocessor 3382, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 3389 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 3390 or an electrode on another lead serving as a ground electrode. Some embodiments may have multiple can electrodes such as may be used to sense electrocardiograms (ECGs). Some embodiments provide a shock pulse generator 3391 interfaced to the controller for delivering a defibrillation shock via shock electrodes 3392 and 3393 to the atria or ventricles upon detection of a shockable tachyarrhythmia.

Neural stimulation channels, identified as channels D and E, are incorporated into the device for delivering parasympathetic and/or sympathetic excitation and/or parasympathetic and/or sympathetic inhibition, where one channel includes a bipolar lead with a first electrode 3394D and a second electrode 3395D, a pulse generator 3396D, and a channel interface 3397D, and the other channel includes a bipolar lead with a first electrode 3394E and a second electrode 3395E, a pulse generator 3396E, and a channel interface 3397E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, frequency, duty-cycle, and the like. In some embodiments, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 3398 connected to the microprocessor, which can be used to communicate with an external device. The illustrated microprocessor 2489 is capable of performing neural stimulation therapy routines and myocardial (CRM) stimulation routines and is also capable of monitoring autonomic health by evaluating subtle and/or inconsistent responses to an ANS dose. Examples of NS therapy routines include, but are not limited to, therapies to provide physical conditioning and therapies to treat ventricular remodeling, hypertension, sleep disordered breathing, blood pressure control such as to treat hypertension, cardiac rhythm management, myocardial infarction and ischemia, heart failure, epilepsy, depression, for pain, migraines, eating disorders and obesity, and movement disorders. Examples of myocardial therapy routines, but are not limited to, include bradycardia pacing therapies, anti-tachycardia shock therapies such as cardioversion or defibrillation therapies (including subcutaneous implantable cardioverter-defibrillators), anti-tachycardia pacing therapies (ATP), and cardiac resynchronization therapies (CRT). Additional sensors (not illustrated) such as respiration and blood pressure sensors may also be incorporated into the system for use in titrating an ANS therapy. An ANS dose routine may be performed to deliver a test dose of stimulation via stimulus 3396D or 3396E, and monitor HR via sensing amplifiers 3386A-C.

Figure 34:
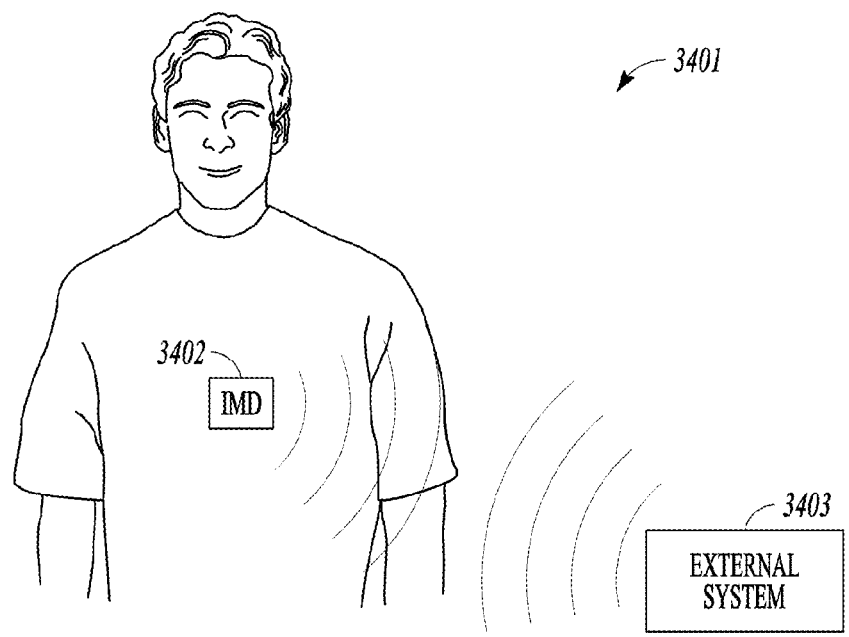
FIG. 34 illustrates a system including an implantable medical device (IMD) and an external system or device, according to various embodiments of the present subject matter.

FIG. 34 illustrates a system 3401 including an implantable medical device (IMD) 3402 and an external system or device 3403, according to various embodiments of the present subject matter. Various embodiments of the IMD include NS functions or include a combination of NS (e.g. ANS dose) and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. The external system allows a user such as a physician or other caregiver or a patient to control the operation of the IMD and obtain information acquired by the IMD. In one embodiment, the external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below. The telemetry link provides for data transmission from the implantable medical device to the external system. This includes, for example, transmitting real-time physiological data acquired by the IMD, extracting physiological data acquired by and stored in the IMD, extracting therapy history data stored in the implantable medical device, and extracting data indicating an operational status of the IMD (e.g., battery status and lead impedance). The telemetry link also provides for data transmission from the external system to the IMD. This includes, for example, programming the IMD to acquire physiological data, programming the IMD to perform at least one self-diagnostic test (such as for a device operational status), and programming the IMD to deliver at least one therapy.

Figure 35:
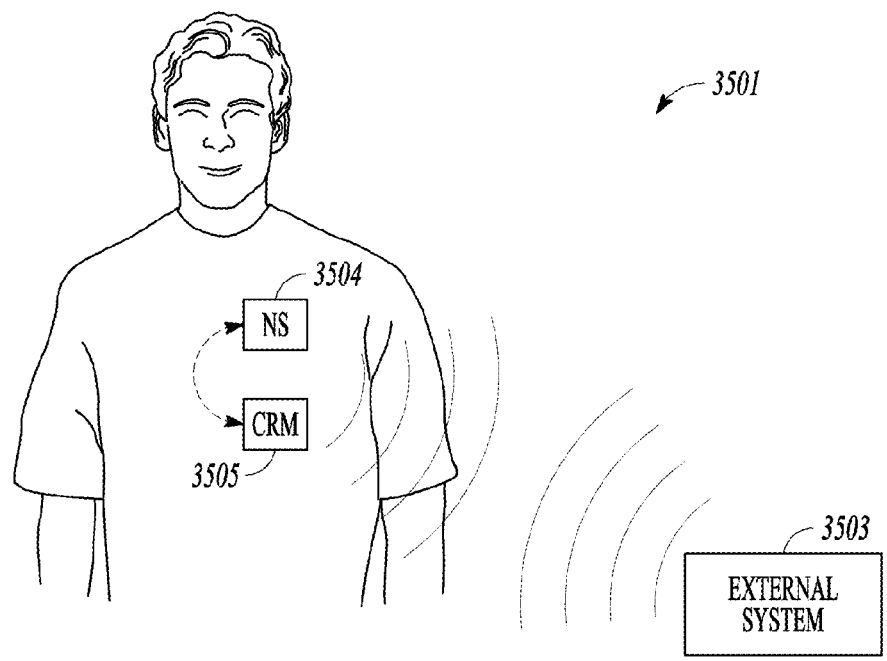
FIG. 35 illustrates a system including an external device, an implantable neural stimulator (NS) device which may be used to provide a NS dose or therapy and an implantable cardiac rhythm management (CRM) device, according to various embodiments of the present subject matter.

FIG. 35 illustrates a system 3501 including an external device 3503, an implantable neural stimulator (NS) device 3504 which may be used to provide a NS dose or therapy and an implantable cardiac rhythm management (CRM) device 3505, according to various embodiments of the present subject matter. The CRM device may be a pacemaker, a cardioverter, a defibrillator, a CRT device, or a subcutaneous implantable cardioverter-defibrillator. Various aspects involve communication between an NS device and a CRM device or other cardiac stimulator. In various embodiments, this communication may allow the NS device to deliver ANS dose to monitor autonomic health or may allow one of the devices 2613 or 2614 to deliver more appropriate therapy (i.e. more appropriate NS therapy or CRM therapy) based on data received from the other device. Additionally, the sensors from the CRM device may monitor HR, BP, or another parameter for the response to the neural stimulation. Some embodiments provide on-demand communications. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

FIGS. 36-39 illustrate system embodiments adapted to provide vagal stimulation, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve, and various embodiments may deliver non-selective bidirectional stimulation of the nerve fibers. The ANS dose may be delivered to the right and/or left vagus nerve. Those of ordinary skill in the art will also understand, upon reading and comprehending this disclosure, that similar systems may be designed to stimulate other ANS targets such as, by way of example and not limitation the carotid sinus nerve, the glossopharyngeal nerve, baroreceptor regions, and chemoreceptor regions.

Figure 36:
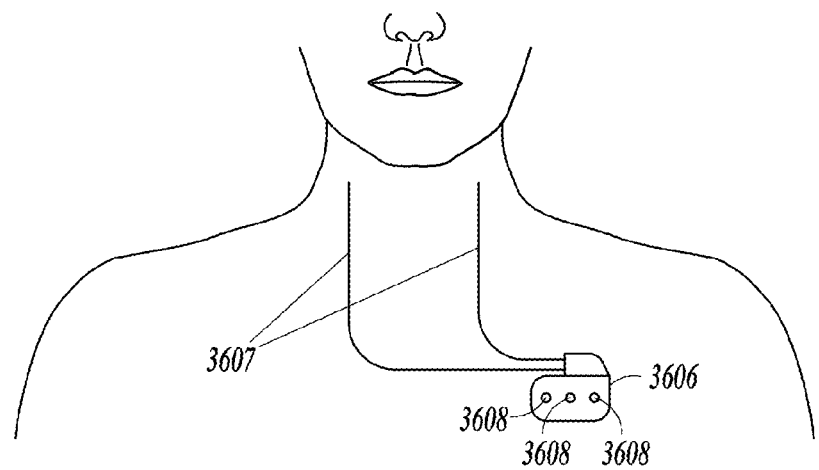
FIG. 36 illustrates a system embodiment in which an IMD is placed subcutaneously or submuscularly in a patient's chest with lead(s) 3607 positioned to stimulate a vagus nerve.

FIG. 36 illustrates a system embodiment in which an IMD 3606 is placed subcutaneously or submuscularly in a patient's chest with lead(s) 3607 positioned to stimulate a vagus nerve. According to various embodiments, neural stimulation lead(s) 3607 are subcutaneously tunneled to a neural target, and can have a nerve cuff electrode to stimulate the neural target or may have electrode(s) place proximately within the carotid sheath. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes 3608 on the housing of the device. These ECG electrodes are capable of being used to detect R-R intervals, PQRS waveforms, or heart rate, for example.

Figure 37:
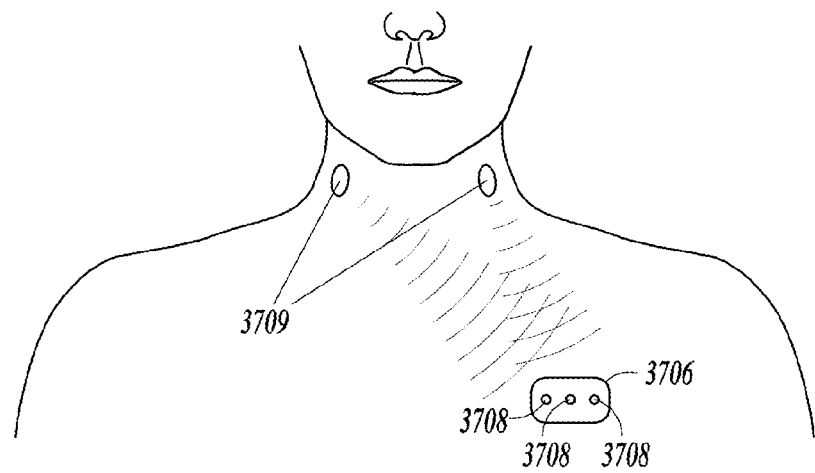
FIG. 37 illustrates a system embodiment that includes an implantable medical device (IMD) with satellite electrode(s) positioned to stimulate at least one neural target.

FIG. 37 illustrates a system embodiment that includes an implantable medical device (IMD) 3706 with satellite electrode(s) 3709 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 3708 are capable of being used to detect R-R intervals, PQRS waveforms, or heart rate, for example.

Figure 38:
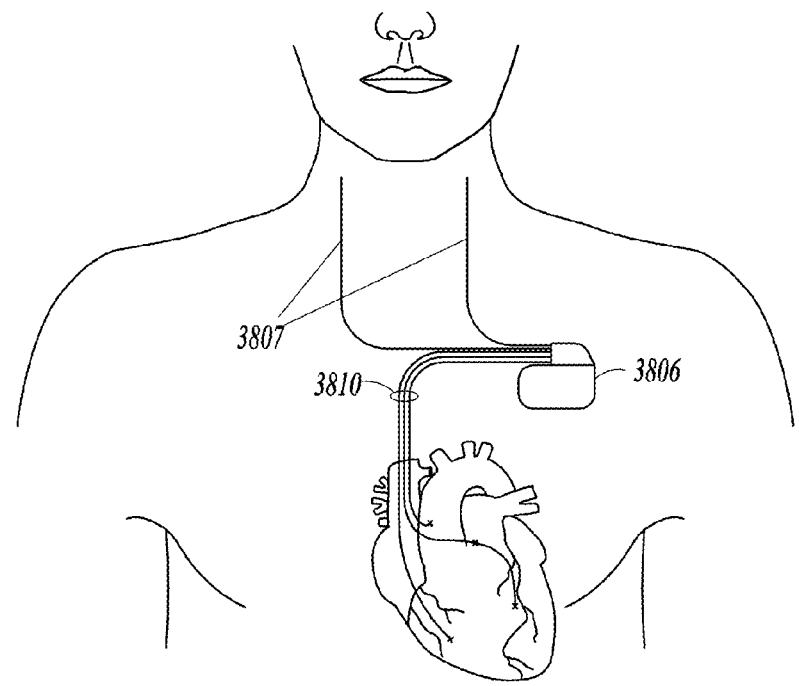
FIG. 38 illustrates an IMD placed subcutaneously or submuscularly in a patient's chest with lead(s) positioned to provide a CRM therapy to a heart, and with lead(s) positioned to stimulate and/or inhibit neural traffic at a neural target, such as a vagus nerve, according to various embodiments.

FIG. 38 illustrates an IMD 3806 placed subcutaneously or submuscularly in a patient's chest with lead(s) 3810 positioned to provide a CRM therapy to a heart, and with lead(s) 3807 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 39:
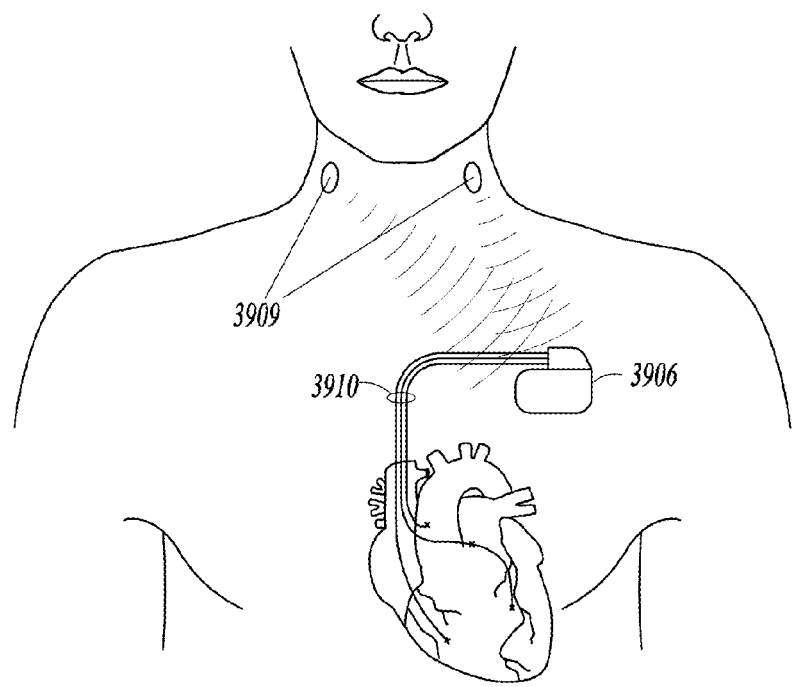
FIG. 39 illustrates an IMD with lead(s) positioned to provide a CRM therapy to a heart, and with satellite transducers positioned to stimulate/inhibit a neural target such as a vagus nerve, according to various embodiments.

FIG. 39 illustrates an IMD 3906 with lead(s) 3910 positioned to provide a CRM therapy to a heart, and with satellite transducers 3909 positioned to stimulate/inhibit a neural target such as a vagus nerve, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 40:
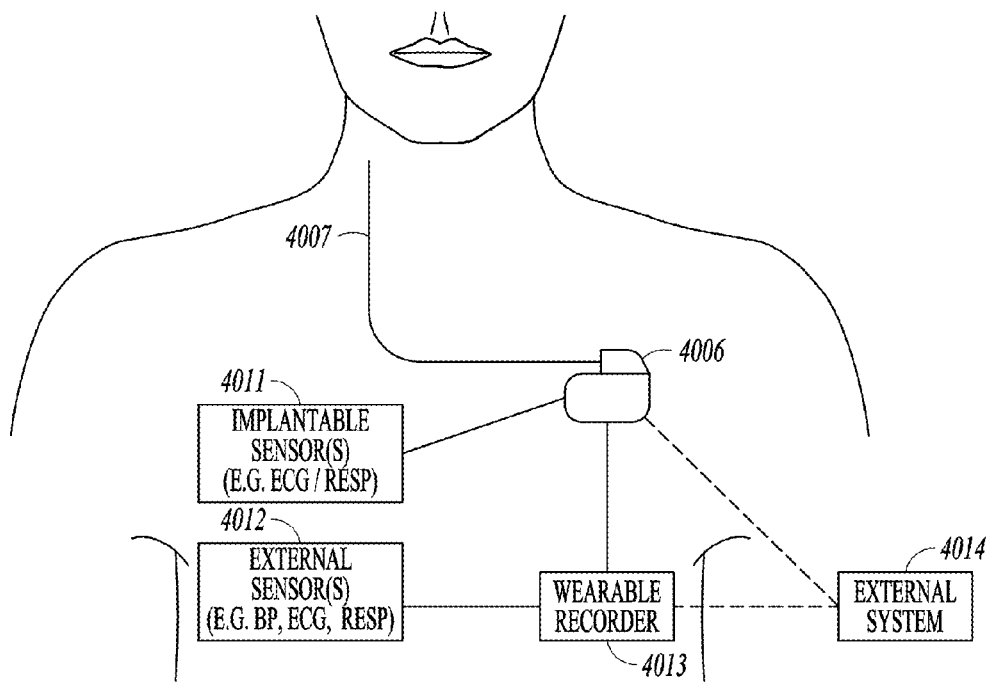
FIG. 40 illustrates, by way of example, an IMD with a lead positioned to stimulate and/or inhibit neural traffic at a vagus nerve, according to various embodiments.

FIG. 40 illustrates, by way of example, an IMD 4006 with a lead 4007 positioned to stimulate and/or inhibit neural traffic at a vagus nerve, according to various embodiments. Some embodiments may use implantable sensor(s) 4011, such as ECG or respiratory sensors, to sense physiological parameters for use in detecting the subtle and/or inconsistent physiological response. Sensed data from the implantable sensor(s) may be recorded in the IMD 4006. Some embodiments may use external sensor(s) 4012, such as blood pressure, ECG or respiratory sensor, to sense physiological parameters for use in detecting the subtle physiological response. Sensed data from the external sensor(s) 4012 may be recorded in an external recorder such as a wearable recorder 4013. In some embodiments, the wearable recorder 4013 may communicate with the IMD 4006. In some embodiments, the wearable recorder may communicate with an external system 4014 such as but not limited to a programmer. In some embodiments, the IMD 4006 may communicate with an external system 4014 such as but not limited to a programmer.

Figure 41:
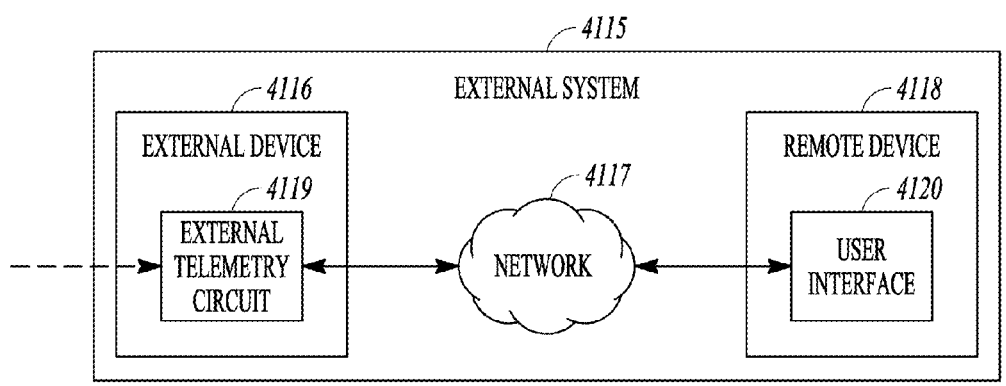
FIG. 41 is a block diagram illustrating an embodiment of an external system.

FIG. 41 is a block diagram illustrating an embodiment of an external system 4115. The external system includes a programmer, in some embodiments. In the illustrated embodiment, the external system includes a patient management system. As illustrated, the external system 4115 is a patient management system including an external device 4116, a telecommunication network 4117, and a remote device 4118. The external device 4115 is placed within the vicinity of an implantable medical device (IMD) and includes an external telemetry system 4119 to communicate with the IMD. The remote device(s) 4118 is in one or more remote locations and communicates with the external device 4116 through the network 4117, thus allowing a physician or other caregiver to monitor and treat a patient from a distant location and/or allowing access to various treatment resources from the one or more remote locations. The illustrated remote device 4118 includes a user interface 4120. According to various embodiments, the external device 4116 includes a neural stimulator, a programmer or other device such as a computer, a personal data assistant or phone. The external device 4116, in various embodiments, includes two devices adapted to communicate with each other over an appropriate communication channel. The external device can be used by the patient or physician to provide side effect feedback indicative of patient discomfort, for example.

Patient management systems may be used to enable the patient and/or doctor to monitor autonomic health, and may be used to adjust parameter(s) to compensate for undesired responses, such as may be sensed by physiologic parameters and output to the patient and/or doctor. The inputs may be provided by computers, programmers, cell phones, personal digital assistants, and the like. The patient may call a call center using a regular telephone, a mobile phone, or the Internet. The communication can be through a repeater, similar to that used in Boston Scientific's Latitude patient management system. In response, the call center (e.g. server in call center) may automatically send information to the device to adjust or titrate the therapy. The call center may inform the patient's physician of the event. A device interrogation may be automatically triggered. The results of the device interrogation may be used to determine if and how the therapy should be adjusted and/or titrated to improve the response. A server can automatically adjust and/or titrate the therapy using the results of the device interrogation. Medical staff may review the results of the device interrogation, and program the device through the remote server to provide the desired therapy adjustments and/or titrations. The server may communicate results of the device interrogation to the patient's physician, who may provide input or direction for adjusting and/or titrating the therapy.

Figure 42:
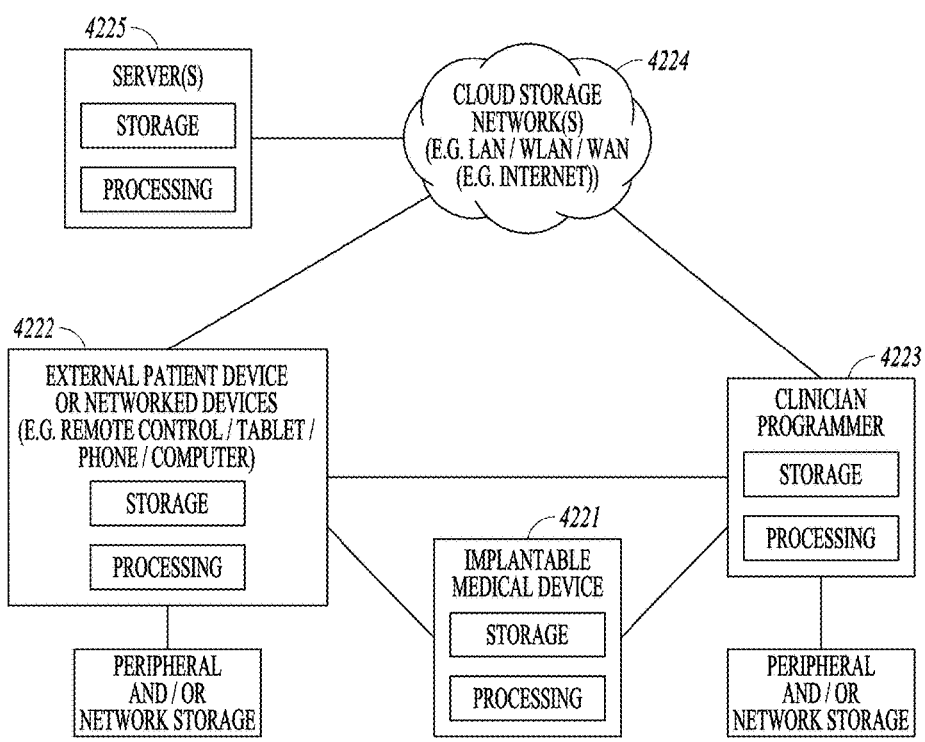
FIG. 42 illustrates, by way of example and not limitation, an embodiment of a system, various components of which may be used to store the population data and process the population data to score the data.

FIG. 42 illustrates, by way of example and not limitation, an embodiment of a system, various components of which may be used to store the population data and process the population data to score the data. The illustrated system may include an implantable device 4221, an external device 4222, a clinician programmer 4223, a network 4224 and server(s) 4225 connected through the network. Any one or combination of the devices may store data, and any one or combination of the devices may process the data. Furthermore, by way of example, the external patient device 4222 and/or the clinician programmer may be connected to the same or different storage.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. A system may be configured to implement the method. The system may be configured with hardware, software, firmware, or any combination thereof to implement the method. In various embodiments, the methods are implemented using computer data in tangible media, that represents a sequence of instructions which, when executed by one or more processors cause the processor(s) to perform the respective method or at least a portion of the method. In various embodiments, the methods are implemented as a set (or sets) of instructions contained on a computer-accessible medium (or media) capable of directing a processor or other controller to perform the respective method or at least a portion of the method. In various embodiments, the medium or media include at least one of a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
   delivering an autonomic neural stimulation (ANS) dose over a plurality of burst periods, including delivering a burst stimulation pulses within a portion of each burst period to evoke physiological responses and not delivering stimulation pulses within another portion of each burst period;
   recording physiological parameter values, including:
      recording first population data, the first population data including evoked response (ER) values corresponding to the evoked physiological responses to the burst of stimulation pulses for the plurality of burst periods; and
      recording second population data, the second population data including reference values that include no effect (NE) values corresponding to times without an evoked physiological response;
   calculating evoked response metrics (ERMs) using the first and second population data, each of the ERMs being dependent on background autonomic activity;
   analyzing the ERMs to provide ERM analysis; and
   providing an indication of autonomic health using the ERM analysis.

2. The method of claim 1, wherein analyzing the ERMs includes comparing the ERMs to at least one reference value to provide the ERM analysis used to provide the indication of autonomic health.

3. The method of claim 1, wherein analyzing the ERMs includes trending the ERMs to provide the ERM analysis used to provide the indication of autonomic health.

4. The method of claim 1, wherein the ER values include:
   stimulation effect (SE) values corresponding to direct responses to delivered stimulation pulses; or
   reflex effect (RE) values corresponding to reflex responses after delivered stimulation pulses; or
   both SE values and RE values.

5. The method of claim 1, wherein delivering the ANS dose includes delivering bursts of neural stimulation pulses, the NE values including values during times between successive bursts of neural stimulation pulses.

6. The method of claim 1, wherein the physiological parameter values include at least one of: heart rate values or heart rate variability values.

7. The method of claim 1, wherein the physiological parameter values include at least one of: respiratory values or respiratory variability values.

8. The method of claim 1, wherein the physiological parameter values include at least one of: blood pressure values or blood pressure variability values.

9. The method of claim 1, wherein recording physiological parameter values includes recording electrocardiograms (ECGs), and calculating ERMs includes calculating ERMs using a statistical analysis of at least one feature of the ECGs.

10. The method of claim 1, wherein calculating ERMs includes:
    Z-scoring groups of recorded physiological parameter values to obtain Z-scores for each of the groups; or
    T-scoring groups of recorded physiological parameter values to obtain T-scores for each of the groups.

11. The method of claim 1, wherein delivering the ANS dose includes delivering neural stimulation to a vagus nerve.

12. The method of claim 1, wherein delivering the ANS dose includes delivering neural stimulation to a carotid sinus nerve or a glossopharyngeal nerve.

13. The method of claim 1, wherein delivering the ANS dose includes delivering neural stimulation to a baroreceptor region or to a chemoreceptor region.

14. A method, comprising:
    delivering a vagal nerve stimulation (VNS) dose over a plurality of burst periods, the VNS dose including a plurality of stimulation bursts, each stimulation burst including a plurality of neural stimulation pulses within a portion of each burst period and another portion of each period does not include neural stimulation pulses;

sensing heart rate and recording heart rate values, including:
- recording first population data, the first population data including evoked response (ER) values corresponding to the evoked heart rate effects to stimulation bursts for the plurality of burst periods; and
- recording second population data, the second population data including reference values that include no effect (NE) values corresponding to heart rate values that are not evoked heart rate responses to stimulation bursts;

calculating evoked response metrics (ERMs) to quantify a relationship between the first population data and the second population data, each of the ERMs being dependent on background sympathetic activity;

analyzing the ERMs to provide ERM analysis; and providing an indication of autonomic health using the ERM analysis.

15. The method of claim 14, further comprising adjusting the ANS dose in steps, calculating an ERM for each step and comparing the ERM to a reference value to monitor autonomic health.

16. The method of claim 14, wherein analyzing the ERMs includes comparing the ERMs to at least one reference value to provide the ERM analysis used to provide the indication of autonomic health.

17. The method of claim 14, wherein analyzing the ERMs includes trending the ERMs to provide the ERM analysis used to provide the indication of autonomic health.

18. The method of claim 14, further comprising detecting a patient status or a patient condition, and tagging the ERMs with the detected patient status or condition.

19. The method of claim 14, wherein:
the ER values in the first population data include stimulation effect (SE) values corresponding to direct responses to stimulation bursts; and
calculating ERMs includes analyzing for a SE signature.

20. The method of claim 14, wherein:
the ER values in the first population data include reflex effect (RE) values corresponding to reflex responses after stimulation bursts; and
calculating the ERM to quantify the relationship between the first population data and the second population data includes analyzing for a RE signature.

* * * * *